(12) United States Patent
Lee et al.

(10) Patent No.: US 11,318,167 B2
(45) Date of Patent: May 3, 2022

(54) ISOLATION OF FUSION-COMPETENT MYOBLASTS AND THERAPEUTIC APPLICATIONS THEREOF RELATED TO MUSCULAR DYSTROPHY

(71) Applicant: THE JOHNS HOPKINS UNIVERSITY, Baltimore, MD (US)

(72) Inventors: Gabsang Lee, Ellicott City, MD (US); InYoung Choi, Baltimore, MD (US); HoTae Lim, Baltimore, MD (US); Kathryn R. Wagner, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 678 days.

(21) Appl. No.: 15/781,709

(22) PCT Filed: Dec. 9, 2016

(86) PCT No.: PCT/US2016/065704
§ 371 (c)(1),
(2) Date: Jun. 6, 2018

(87) PCT Pub. No.: WO2017/100498
PCT Pub. Date: Jun. 15, 2017

(65) Prior Publication Data
US 2018/0360887 A1    Dec. 20, 2018

Related U.S. Application Data

(60) Provisional application No. 62/266,181, filed on Dec. 11, 2015.

(51) Int. Cl.
*A61K 35/34* (2015.01)
*C12N 5/00* (2006.01)
(Continued)

(52) U.S. Cl.
CPC ............ *A61K 35/34* (2013.01); *A61K 35/545* (2013.01); *A61P 21/00* (2018.01); *C12N 5/0658* (2013.01);
(Continued)

(58) Field of Classification Search
CPC .. A61K 35/34; C12N 5/0658; C12N 2501/00; C12N 2506/00
See application file for complete search history.

(56) References Cited

U.S. PATENT DOCUMENTS 10,240,123 B2 †  3/2019  Pourquie
10,620,109 B2 *  4/2020  Saito et al. ........ G01N 15/1434
(Continued)

FOREIGN PATENT DOCUMENTS

EP    2606884 A1    6/2013
EP    3286301 A1    2/2018
(Continued)

OTHER PUBLICATIONS

Borchin et al. "Derivation and FACS-Mediated Purification of PAX3+/PAX7+ Skeletal Muscle Precursors from Human Pluripotent Stem Cells" Stem Cell Reports, 1 (2013), pp. 620-631. (Year: 2013).*

(Continued)

*Primary Examiner* — James D Schultz
*Assistant Examiner* — James Joseph Graber
(74) *Attorney, Agent, or Firm* — Mintz Levin Cohn Ferris Glovsky and Popeo, P.C.; Peter F. Corless

(57) ABSTRACT

Described are methods of isolating high purity myoblasts that are used to create novel DMD model systems and methods using human induced pluripotent stem cells (hiPSCs). Also described are therapeutic methods based on the use of these myoblasts.

7 Claims, 12 Drawing Sheets
(10 of 12 Drawing Sheet(s) Filed in Color)

(51) Int. Cl.
*A61P 21/00* (2006.01)
*A61K 35/545* (2015.01)
*C12N 5/077* (2010.01)
*G01N 33/50* (2006.01)

(52) U.S. Cl.
CPC .... *G01N 33/5073* (2013.01); *C12N 2501/115* (2013.01); *C12N 2501/415* (2013.01); *C12N 2501/727* (2013.01); *C12N 2501/999* (2013.01); *C12N 2503/02* (2013.01); *C12N 2506/02* (2013.01); *C12N 2506/45* (2013.01)

(56) References Cited

U.S. PATENT DOCUMENTS

| | | |
|---|---|---|
| 2013/0302824 A1 | 11/2013 | Klimanskaya et al. |
| 2015/0125952 A1 | 5/2015 | Kim et al. |
| 2015/0191699 A1 | 7/2015 | Wang et al. |
| 2015/0376646 A1 | 12/2015 | Flynn et al. |
| 2017/0342373 A1 | 11/2017 | Wan et al. |

FOREIGN PATENT DOCUMENTS

| | | | | |
|---|---|---|---|---|
| JP | 2015005447 | * | 1/2016 | .......... A61K 31/405 |
| WO | 2013108039 A1 | | 7/2013 | |
| WO | 2013138623 A1 | | 9/2013 | |
| WO | 2015066377 A1 | | 5/2015 | |
| WO | 2017100498 A1 | | 12/2015 | |
| WO | WO2016168890 A1 | * | 10/2016 | ............. C12N 5/077 |

OTHER PUBLICATIONS

Webster et al. "Isolation of Human Myoblasts with the Fluorescence-Activated Cell Sorter", Experimental Cell Research 174 (1988) 252-265. (Year: 1988).*
Chai et al. "Differentiation of pluripotent stem cells to muscle fiber to model Duchenne muscular dystrophy" Nature Biotechnology (Sep. 2015), vol. 33, No. 9, pp. 962-969. (Year: 2015).*
Kazuki et al. "Complete Genetic Correction of iPS Cells From Duchenne Muscular Dystrophy" Molecular Therapy (2010), vol. 18, No. 2, pp. 386-393. (Year: 2010).*
Wang et al. "Wnt/β-catenin signaling controls Mespo expression to regulate segmentation during Xenopus somitogenesis" Developmental Biology 304 (2007) 836-847. (Year: 2007).*
Romorini et al. "AKT/GSK3β signaling pathway is critically involved in human pluripotent stem cell survival" Sci Rep 6, 35660, 15 pages (Oct. 2016). (Year: 2016).*
Mayeuf-Louchart et al. "Notch regulation of myogenic versus endothelial fates of cells that migrate from the somite to the limb", PNAS (Jun. 2014), vol. 111, No. 24, 8844-8849. (Year: 2014).*
Shelton et al. "Derivation and Expansion of PAX7-Positive Muscle Progenitors from Human and Mouse Embryonic Stem Cells" Stem Cell Reports (Sep. 2014), vol. 3. 516-529. (Year: 2014).*
R&D Systems, "N-2 Plus Media Supplement", accessed Jul. 15, 2021, retrieved from: https://www.rndsystems.com/products/n-2-plus-media-supplement. (Year: 2021).*
Borchin, B., et al., "Derivation and FACS-Mediated Purification of PAX3+/PAX7+ Skeletal Muscle Precursors from Human Pluripotent Stem Cells", Stem Cell Reports, vol. 1, pp. 620-631, Dec. 17, 2013.
Choi, Y., et al., "Concordant but Varied Phenotypes among Duchenne Muscular Dystrophy Patient-Specific Myoblasts Derived using a Human iPSC-Based Model", Cell Reports, vol. 15, pp. 2301-2312, Jun. 7, 2016.
Goldstein, J., et al., "SMAD signaling drives heart and muscle dysfunction in a *Drosophila* model of muscular dystrophy". Human Molecular Genetics, (2011) vol. 20, No. 5, pp. 894-904.
Kazuki, Y., et al., "Complete Genetic Correction of iPS Cells From Duchenne Muscular Dystrophy", Molecular Therapy, (2010) vol. 18, No. 2, pp. 386-393.
Kazuki, et al., Complete genetic correction of ips cells from Duchenne muscular dystrophy. Mol Ther. Feb. 2010;18(2):386-93.

Borchin, et al., Derivation and FACS-mediated purification of PAX3+/PAX7+ skeletal muscle precursors from human pluripotent stem cells. Stem Cell Reports. Nov. 27, 2013;1(6):620-31.
Liu, et al., Timely inhibition of Notch signaling by DAPT promotes cardiac differentiation of murine pluripotent stem cells. PLoS One. Oct. 14, 2014;9(10):e109588.
Goldstein, et al., SMAD signaling drives heart and muscle dysfunction in a *Drosophila* model of muscular dystrophy. Hum Mol Genet. Mar. 1, 2011;20(5):894-904.
Marg, et al., Human satellite cells have regenerative capacity and are genetically manipulable. J Clin Invest. Oct. 2014;124(10):4257-65.
Choi, et al., Concordant but Varied Phenotypes among Duchenne Muscular Dystrophy Patient-Specific Myoblasts Derived using a Human iPSC-Based Model. Cell Rep. Jun. 7, 2016;15(10):2301-2312.
Abujarour, et al., Myogenic differentiation of muscular dystrophy-specific induced pluripotent stem cells for use in drug discovery. Stem Cells Transl Med. Feb. 2014;3(2):149-60.
Bain, et al., The selectivity of protein kinase inhibitors: a further update. Biochem J. Dec. 15, 2007;408(3):297-315.
Barberi, et al., Derivation of engraftable skeletal myoblasts from human embryonic stem cells. Nat Med. May 2007;13(5):642-8.
Bennett, et al., Regulation of Wnt signaling during adipogenesis. J Biol Chem. Aug. 23, 2002;277(34):30998-1004.
Blauwkamp, et al., Endogenous Wnt signalling in human embryonic stem cells generates an equilibrium of distinct lineage-specified progenitors Nat Commun. 2012;3:1070.
Borowaik, et al., Small molecules efficiently direct endodermal differentiation of mouse and human embryonic stem cells. Cell Stem Cell. Apr. 3, 2009;4(4):348-58.
Brennand, et al., Modelling schizophrenia using human induced pluripotent stem cells. Nature. May 12, 2011;473(7346):221-5.
Burridge, et al., Chemically defined generation of human cardiomyocytes. Nat Methods. Aug. 2014;11(8):855-60.
Chambers, et al., Highly efficient neural conversion of human ES and iPS cells by dual inhibition of SMAD signaling. Nat Biotechnol. Mar. 2009;27(3):275-80.
Chen, et al., Modeling ALS with iPSCs reveals that mutant SOD1 misregulates neurofilament balance in motor neurons. Cell Stem Cell. Jun. 5, 2014;14(6):796-809.
Choi, et al., Efficient generation human induced pluripotent stem cells from human somatic cells with Sendai-virus. J Vis Exp Apr. 23, 2014;(86).
Darabi, et al., Human ES- and iPS-derived myogenic progenitors restore DYSTROPHIN and improve contractility upon transplantation in dystrophic mice. Cell Stem Cell. May 4, 2012;10(5):610-9.
De Boer, et al., Genetic validation of a therapeutic target in a mouse model of ALS. Sci Transl Med. Aug. 6, 2014;6(248):248ra104.
Delaporte, et al., Comparison between the growth pattern of cell cultures from normal and Duchenne dystrophy muscle. J Neurol Sci. May 1984;64(2):149-60.
Dequeant, et al., Segmental patterning of the vertebrate embryonic axis. Nat Rev Genet. May 2008;9(5):370-82.
Di Giorgio, et al., Human embryonic stem cell-derived motor neurons are sensitive to the toxic effect of glial cells carrying an ALS-causing mutation. Cell Stem Cell. Dec. 4, 2008;3(6):637-48.
Donnelly, et al., Limited availability of ZBP1 restricts axonal mRNA localization and nerve regeneration capacity. EMBO J. Sep. 30, 2011;30(22):4665-77.
Donnelly, et al., RNA toxicity from the ALS/FTD C9ORF72 expansion is mitigated by antisense intervention. Neuron. Oct. 16, 2013;80(2):415-28.
Dovey, et al., Functional gamma-secretase inhibitors reduce beta-amyloid peptide levels in brain. J Neurochem. Jan. 2001;76(1):173-81.
Fior, et al., The differentiation and movement of presomitic mesoderm progenitor cells are controlled by Mesogenin 1. Development. Dec. 15, 2012; 139(24): 4656-4665.
Gussoni, et al., Normal dystrophin transcripts detected in Duchenne muscular dystrophy patients after myoblast transplantation. Nature. Apr. 2, 1992;356(6368):435-8.

(56) References Cited

OTHER PUBLICATIONS

Hoffman, et al., Dystrophin: the protein product of the Duchenne muscular dystrophy locus. Cell. Dec. 24, 1987;51(6):919-28.
Jasmin, et al., Impaired muscle differentiation in explant cultures of Duchenne muscular dystrophy. Lab Invest. Feb. 1984;50(2):197-207.
Jones, et al., Facioscapulohumeral muscular dystrophy family studies of DUX4 expression: evidence for disease modifiers and a quantitative model of pathogenesis. Hum Mol Genet. Oct. 15, 2012;21(20):4419-30.
Karpati, et al., Myoblast transfer in Duchenne muscular dystrophy. Ann Neurol. Jul. 1993;34(1):8-17.
Kiskinis, et al., Pathways disrupted in human ALS motor neurons identified through genetic correction of mutant SOD1. Cell Stem Cell. Jun. 5, 2014;14(6):781-95.
Kornegay, et al., The paradox of muscle hypertrophy in muscular dystrophy. Phys Med Rehabil Clin N Am. Feb. 2012;23(1):149-72, xii.
L'Honore, et al., Sequential expression and redundancy of Pitx2 and Pitx3 genes during muscle development. Dev Biol. Jul. 15, 2007;307(2):421-33.
Lee, et al., Derivation of neural crest cells from human pluripotent stem cells. Nat Protoc. Apr. 2010;5(4):688-701.
Mali, et al., RNA-Guided Human Genome Engineering via Cas9. Science. Feb. 15, 2013; 339(6121): 823-826.
Martin, et al., Myocyte enhancer factor (MEF) 2C: a tissue-restricted member of the MEF-2 family of transcription factors. Proc Natl Acad Sci U S A. Jun. 1, 1993; 90(11): 5282-5286.
Mayeuf-Louchart, et al., Notch regulation of myogenic versus endothelial fates of cells that migrate from the somite to the limb. Proc Natl Acad Sci U S A. Jun. 17, 2014;111(24):8844-9.
Mendell, et al., Myoblast transfer in the treatment of Duchenne's muscular dystrophy. N Engl J Med. Sep. 28, 1995;333(13):832-8.
Millay, et al., Myomaker: A membrane activator of myoblast fusion and muscle formation. Nature. Jul. 18, 2013; 499(7458): 301-305.
Mourikis, et al., Cell-autonomous Notch activity maintains the temporal specification potential of skeletal muscle stem cells. Development. Dec. 2012;139(24):4536-48.
Partridge, The mdx mouse model as a surrogate for Duchenne muscular dystrophy. FEBS J. Sep. 2013;280(17):4177-86.
Scott, et al., Viral vectors for gene transfer of micro-, mini-, or full-length dystrophin. Neuromuscul Disord. Oct. 2002;12 Suppl 1:S23-9.
Skuk, et al., First test of a "high-density injection" protocol for myogenic cell transplantation throughout large volumes of muscles in a Duchenne muscular dystrophy patient: eighteen months follow-up. Neuromuscul Disord. Jan. 2007;17(1)38-46.
Sterrenburg, et al., Gene expression profiling highlights defective myogenesis in DMD patients and a possible role for bone morphogenetic protein 4. Neurobiol Dis Jul. 2006;23(1):228-36.
Tedesco, et al., Transplantation of genetically corrected human iPSC-derived progenitors in mice with limb-girdle muscular dystrophy. Sci Transl Med. Jun. 27, 2012;4(140):140ra89.
Wainger, et al., Intrinsic membrane hyperexcitability of amyotrophic lateral sclerosis patient-derived motor neurons. Cell Rep. Apr. 10, 2014;7(1):1-11.
Wang, et al., Wnt/beta-catenin signaling controls Mespo expression to regulate segmentation during Xenopus somitogenesis. Dev Biol. Apr. 15, 2007;304(2):836-47.
Wang, et al., Titin: major myofibrillar components of striated muscle. Proc Natl Acad Sci U S A. Aug. 1979;76(8):3698-702.
Webster, et al., Isolation of human myoblasts with the fluorescence-activated cell sorter. Exp Cell Res. Jan. 1988;174(1):252-65.
Wohlgemuth, et al., The myosin co-chaperone UNC-45 is required for skeletal and cardiac muscle function in zebrafish. Dev Biol. Mar. 15, 2007;303(2):483-92.
Arpke, et al., A new immuno-, dystrophin-deficient model, the NSG-mdx(4Cv) mouse, provides evidence for functional improvement following allogeneic satellite cell transplantation. Stem Cells. Aug. 2013;31(8):1611-20.

Cesana, et al., A long noncoding RNA controls muscle differentiation by functioning as a competing endogenous RNA. Cell. Oct. 14, 2011;147(2):358-69.
Chal, et al., Differentiation of pluripotent stem cells to muscle fiber to model Duchenne muscular dystrophy. Nat Biotechnol. Sep. 2015;33(9):962-9.
Fan, et al., Rapid death of injected myoblasts in myoblast transfer therapy. Muscle Nerve. Jul. 1996;19(7):853-60.
Gussoni, et al., The fate of individual myoblasts after transplantation into muscles of DMD patients. Nat Med. Sep. 1997;3(9):970-7.
Hartel, et al., Impact of prednisone on TGF-beta1 and collagen in diaphragm muscle from mdx mice. Muscle Nerve. Mar. 2001;24(3):428-32.
Ng, et al., Animal Models of Muscular Dystrophy. Prog Mol Biol Transl Sci. 2012; 105: 83-111.
Pegoraro, et al., SPP1 genotype is a determinant of disease severity in Duchenne muscular dystrophy. Neurology. Jan. 18, 2011;76(3):219-26.
Porter, et al., A chronic inflammatory response dominates the skeletal muscle molecular signature in dystrophin-deficient mdx mice. Hum Mol Genet. Feb. 1, 2002;11(3):263-72.
Shelton, et al., Derivation and Expansion of PAX7-Positive Muscle Progenitors from Human and Mouse Embryonic Stem Cells Stem Cell Reports. Sep. 9, 2014; 3(3): 516-529.
Zatz, et al., Milder course in Duchenne patients with nonsense mutations and no muscle dystrophin. Neuromuscul Disord. Nov. 2014;24(11):986-9.
Inoue, et al., iPS cells: a game changer for future medicine. EMBO J. Mar. 3, 2014;33(5):409-17.
Abujarour, et al., Optimized surface markers for the prospective isolation of high-quality hiPSCs using flow cytometry selection Sci Rep. 2013;3:1179.
Beauchamp, et al., Expression of CD34 and Myf5 defines the majority of quiescent adult skeletal muscle satellite cells. J Cell Biol. Dec. 11, 2000;151(6):1221-34.
Bilic, et al., Concise review: Induced pluripotent stem cells versus embryonic stem cells: close enough or yet too far apart? Stem Cells. Jan. 2012;30(1):33-41.
Demestre, et al., Characterization of matrix metalloproteinases in denervated muscle. Neuropathol Appl Neurobiol. Oct. 2005;31(5):545-55.
Gomez, et al., Antibody effector mechanisms in myasthenia gravis-pathogenesis at the neuromuscular junction. Autoimmunity. Aug. 2010;43(5-6):353-70.
Goudenege, et al., Myoblasts Derived From Normal hESCs and Dystrophic hiPSCs Efficiently Fuse With Existing Muscle Fibers Following Transplantation. Mol Ther. Nov. 2012; 20(11): 2153-2167.
Guo, et al., Neuromuscular junction formation between human stem cell-derived motoneurons and human skeletal muscle in a defined system. Biomaterials. Dec. 2011;32(36):9602-11.
Guo, et al., In vitro Differentiation of Functional Human Skeletal Myotubes in a Defined System. Biomater Sci. Jan. 1, 2014; 2(1): 131-138.
Hamill, et al., Improved patch-clamp techniques for high-resolution current recording from cells and cell-free membrane patches. Pflugers Arch. Aug. 1981;391(2):85-100.
Hosoyama, et al., Derivation of myogenic progenitors directly from human pluripotent stem cells using a sphere-based culture. Stem Cells Transl Med. May 2014;3(5):564-74.
Hu, et al., Differentiation of spinal motor neurons from pluripotent human stem cells. Nat Protoc. 2009;4(9):1295-304.
Illing, et al., Definitive Endoderm Formation from Plucked Human Hair-Derived Induced Pluripotent Stem Cells and SK Channel Regulation. Stem Cells Int. 2013;2013:360573.
Jankowski, et al., The role of CD34 expression and cellular fusion in the regeneration capacity of myogenic progenitor cells. J Cell Sci. Nov. 15, 2002;115(Pt 22):4361-74.
Linta, et al., Rat embryonic fibroblasts improve reprogramming of human keratinocytes into induced pluripotent stem cells. Stem Cells Dev Apr. 10, 2012;21(6):965-76.

(56) References Cited

OTHER PUBLICATIONS

Marteyn, et al., Mutant human embryonic stem cells reveal neurite and synapse formation defects in type 1 myotonic dystrophy. Cell Stem Cell. Apr. 8, 2011;8(4):434-44.

Martinou, et al., Characterization of two factors enhancing choline acetyltransferase activity in cultures of purified rat motoneurons. J Neurosci. Oct. 1989;9(10):3645-56.

Muller, et al., Gene transfer demonstrates that muscle is not a primary target for non-cell-autonomous toxicity in familial amyotrophic lateral sclerosis. Proc Natl Acad Sci U S A. Dec. 19, 2006;103(51):19546-51.

Murray, et al., Review: neuromuscular synaptic vulnerability in motor neurone disease: amyotrophic lateral sclerosis and spinal muscular atrophy. Neuropathol Appl Neurobiol. Apr. 2010;36(2):133-56.

Orth, et al., Inclusion formation in Huntington's disease R6/2 mouse muscle cultures. J Neurochem. Oct. 2003;87(1):1-6.

Park, et al., A Comparative Study of Magnetic-Activated Cell Sorting, Cytotoxicity and Preplating for the Purification of Human Myoblasts. Yonsei Med J. Apr. 30, 2006; 47(2): 179-183.

Paulin, et al., Desmin: a major intermediate filament protein essential for the structural integrity and function of muscle. Exp Cell Res. Nov. 15, 2004;301(1):1-7.

Skoglund, et al., Physiological and ultrastructural features of human induced pluripotent and embryonic stem cell-derived skeletal myocytes in vitro. Proc Natl Acad Sci U S A. Jun. 3, 2014; 111(22): 8275-8280.

Sommer, et al., Induced pluripotent stem cell generation using a single lentiviral stem cell cassette. Stem Cells. Mar. 2009;27(3):543-9.

Stern-Streater, et al., Evaluation of the effects of different culture media on the myogenic differentiation potential of adipose tissue- or bone marrow-derived human mesenchymal stem cells. Int J Mol Med. Jan. 2014;33(1):160-70.

Stockmann, et al., The dynactin p150 subunit: cell biology studies of sequence changes found in ALS/MND and Parkinsonian syndromes. J Neural Transm (Vienna). May 2013;120(5):785-98.

Tanaka, et al., Efficient and reproducible myogenic differentiation from human iPS cells: prospects for modeling Miyoshi Myopathy in vitro. PLoS One. Apr. 23, 2013;8(4):e61540.

Wong, et al., Skeletal muscle-restricted expression of human SOD1 causes motor neuron degeneration in transgenic mice. Hum Mol Genet. Jun. 1, 2010;19(11):2284-302.

Zammit, et al., The skeletal muscle satellite cell: the stem cell that came in from the cold. J Histochem Cytochem. Nov. 2006;54(11):1177-91.

Demestre, et al., Formation and characterisation of neuromuscular junctions between hiPSC derived motoneurons and myotubes. Stem Cell Res Sep. 2015;15(2):328-36.

Blauwkamp et al., Endogenous Wnt Signalling in Human Embryonic Stem Cells Generates an Equilibrium of Distinct Ineage-Specified Progenitors, Nat. Comun, 3:1070, Sep. 18, 2012.

Lim et al., Profiling Individual Human Embryonic Stem Cells by Quantitative RT-PCR, J Vis Exp, 87:51408, May 29, 2014.

Ng et al., "Animal Models of Muscular Dystrophy," Prog Mol Biol Transl Sci., Author Manuscript, available in PMC, 105:83-111, May 19, 2016.

Abujarour et al., Optimized Surface Markers for the Prospective Isolation of High-Quality hiPSCs using Flow Cytometry Selection, Sci Rep., 3:1179, Jan. 31, 2013.

De Carvalho et al., Motoneuron Firing in Amyotrophic Lateral Sclerosis (ALS), Front Hum Neurosci., 8:719, Sep. 22, 2014.

Hu et al., "Differentiation of Spinal Motor Neurons from Pluripotent Human Stem Cells," Nat Protoc. 4(9):1295-304, Dec. 4, 2009.

Illing et al., Definitive Endoderm Formation from Plucked Human Hair-Derived Induced Pluripotent Stem Cells and SK Channel Regulation., Stem Cells Int., 2013:360573, Mar. 13, 2013.

Moloney et al., ALS as a Distal Axonopathy: Molecular Mechanisms Affecting Neuromuscular Junction Stability in the Presymptomatic Stages of the Disease., Front Neurosci, 8:252, Aug. 14, 2014.

Goldstein et al., "SMAD Signaling Drives Heart and Muscle Dysfunction in a Drosophila Model of Muscular Dystrophy," Human Molecular Genetics, 20:5, pp. 894-904, Mar. 1, 2011.

Kazuki et al., "Complete Genetic Correction of iPS Cells from Duchenne Muscular Systrophy," Molecular Therapy, 18:2, pp. 386-393, Dec. 8, 2009.

Liu et al., "Timely Inhibition of Notch Signaling by DAPT Promotes Cardiac Differentiation of Murine Pluripotent Stem Cells" Plos One , 9:10, e109588, Oct. 14, 2014.

Marg et al., "Human Satellite Cells have Regenerative Capacity and are Genetically Manipulable," The Journal of Clinical Investigation, 124:10, pp. 4257-4265, Oct. 2014.

Genbank Database, *Homo sapiens* dystrophin (DMD), transcript variant Dp427c, mRNA, NCBI Reference Sequence: NM_000109. 3, Feb. 22, 2019, 13 pages.

Developmental Studies Hybridoma Bank, "5.1H11 Antibody," web page (screen shot captured May 5, 2020).†

Borchin B., et al., "Derivation and FACS-Mediated Purification of PAX3+/PAX7+ Skeletal Muscle Precursors from Human Pluripotent Stem Cells" Stem Cell Reports, 1 (2013), pp. 620-631.†

Chai J., et al., "Differentiation of pluripotent stem cells to muscle fiber to model Duchenne muscular dystrophy," Nature Biotechnology, 33 (2015), pp. 962-969.†

Walsh F.S., et al., "Surface antigen differentiation during human myogenesis in culture," Nature (London) 289 (Jan. 1981), pp. 60-64.†

Webster C., et al., "Isolation of Human Myoblasts with Flourescence-Activated Cell Sorter," Experimental Cell Research, 174 (1988), pp. 252-265.†

\* cited by examiner
† cited by third party

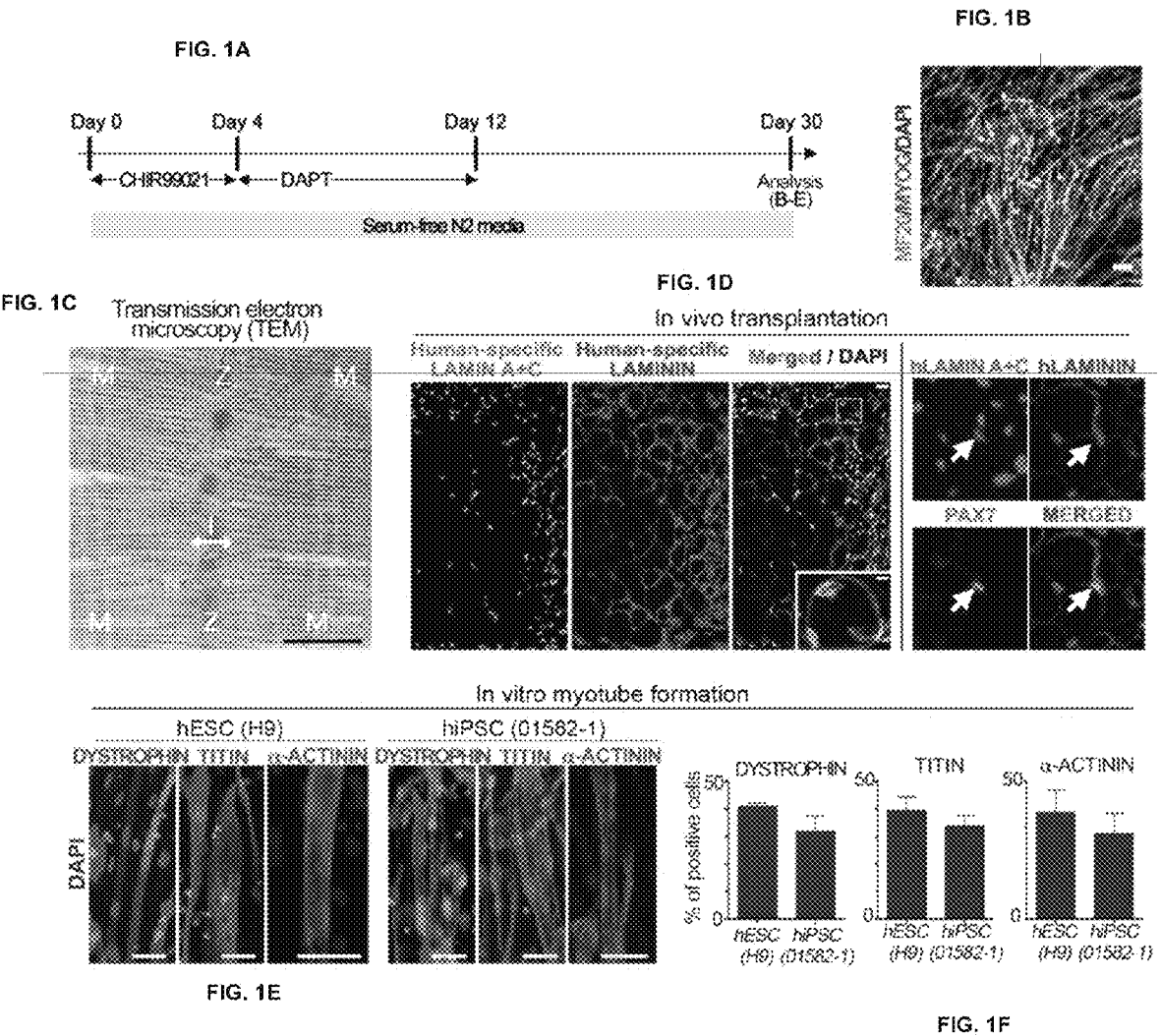

FIG. 2A
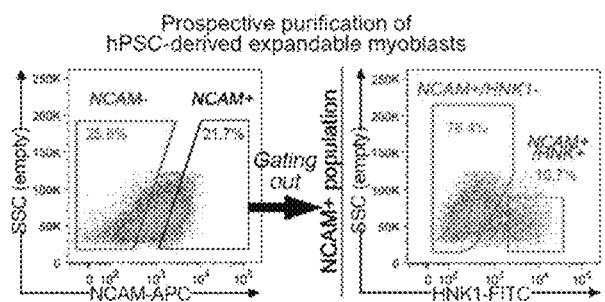
FIG. 2D
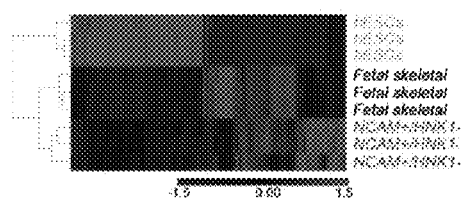
FIG. 2B
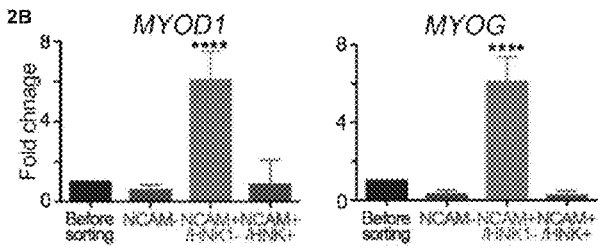
FIG. 2C
FIG. 2F
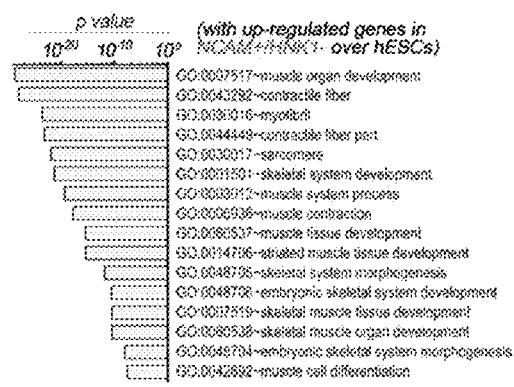
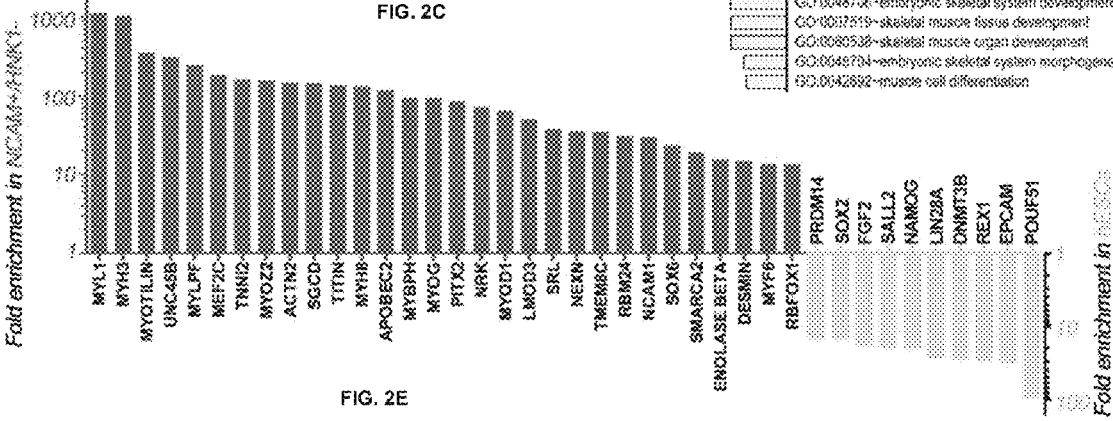
FIG. 2E

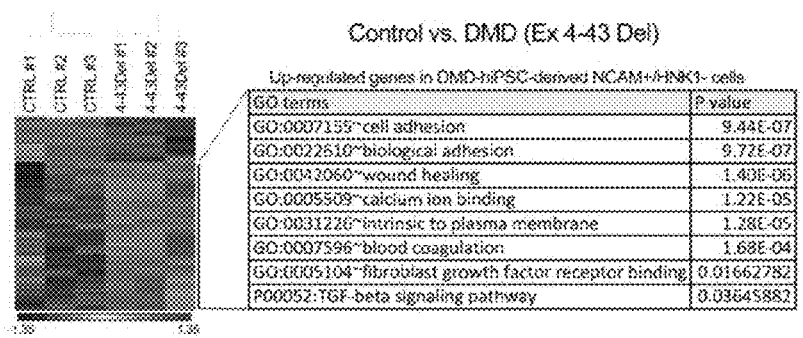
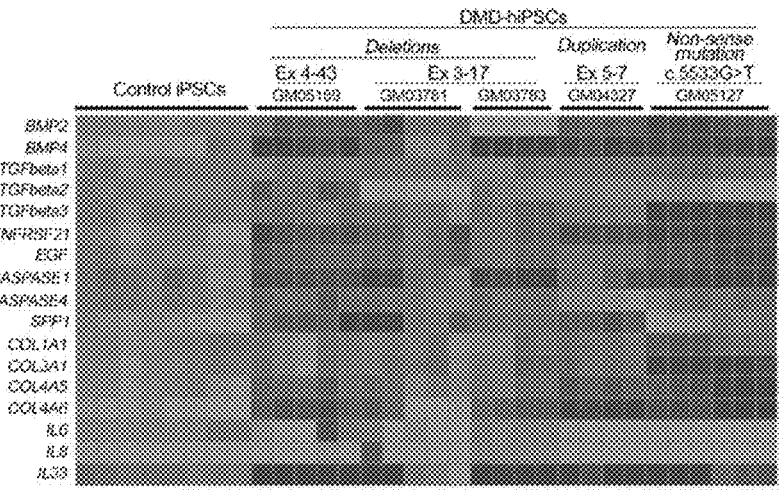
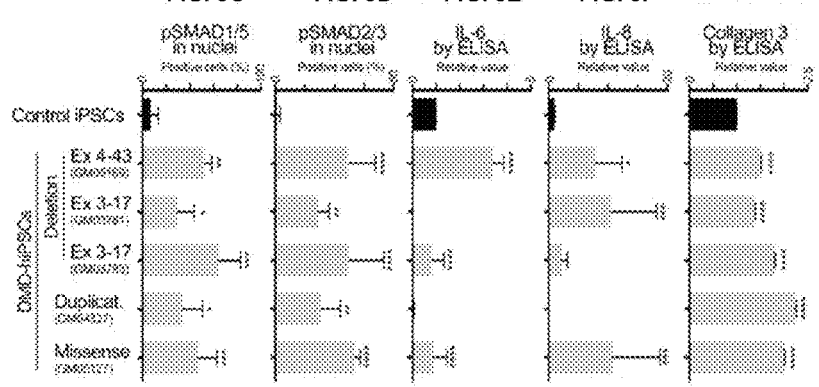

FIG. 4A
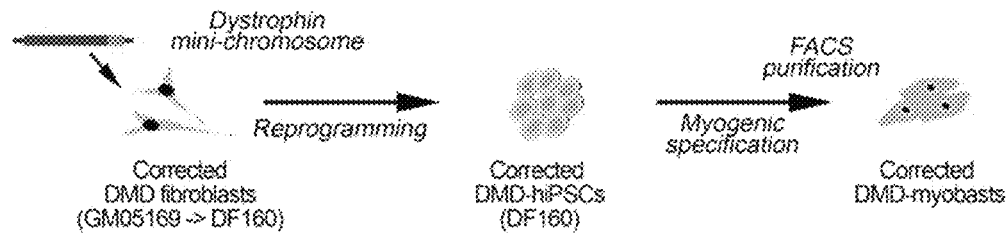
FIG. 4B
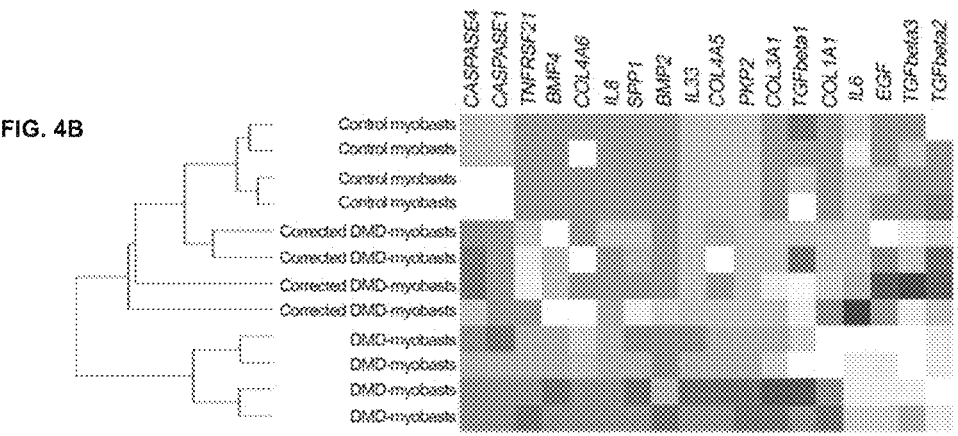
FIG. 4C  FIG. 4D  FIG. 4E  FIG. 4F  FIG. 4G
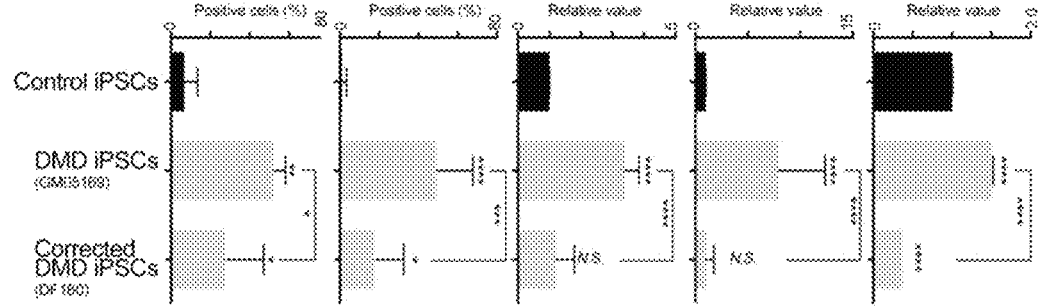
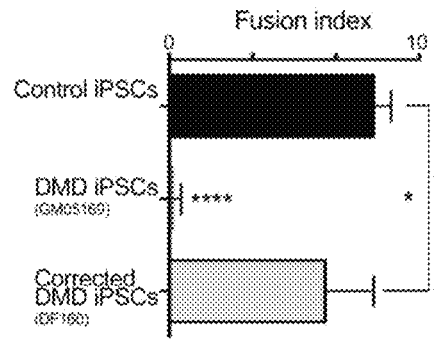
FIG. 4H
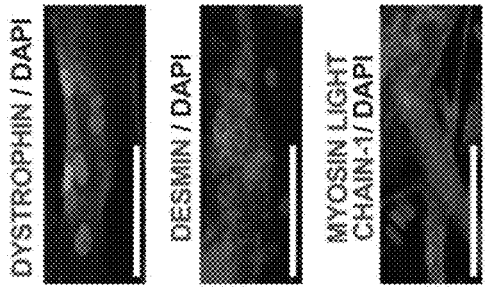
FIG. 4I

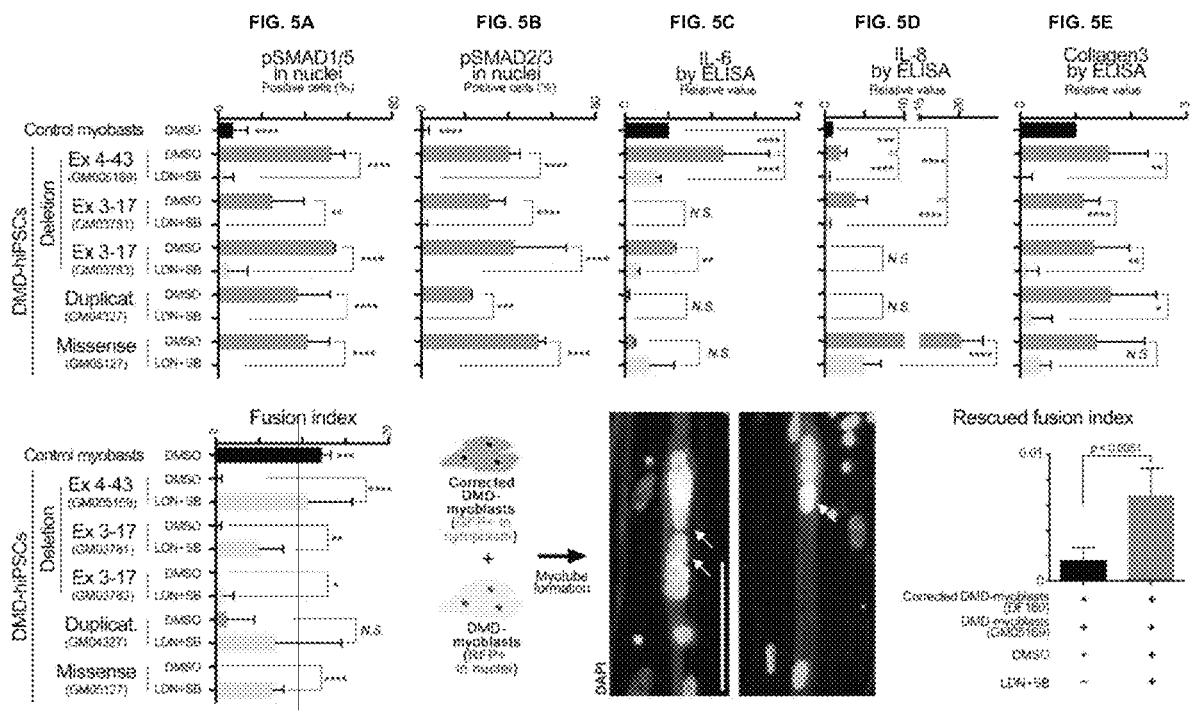

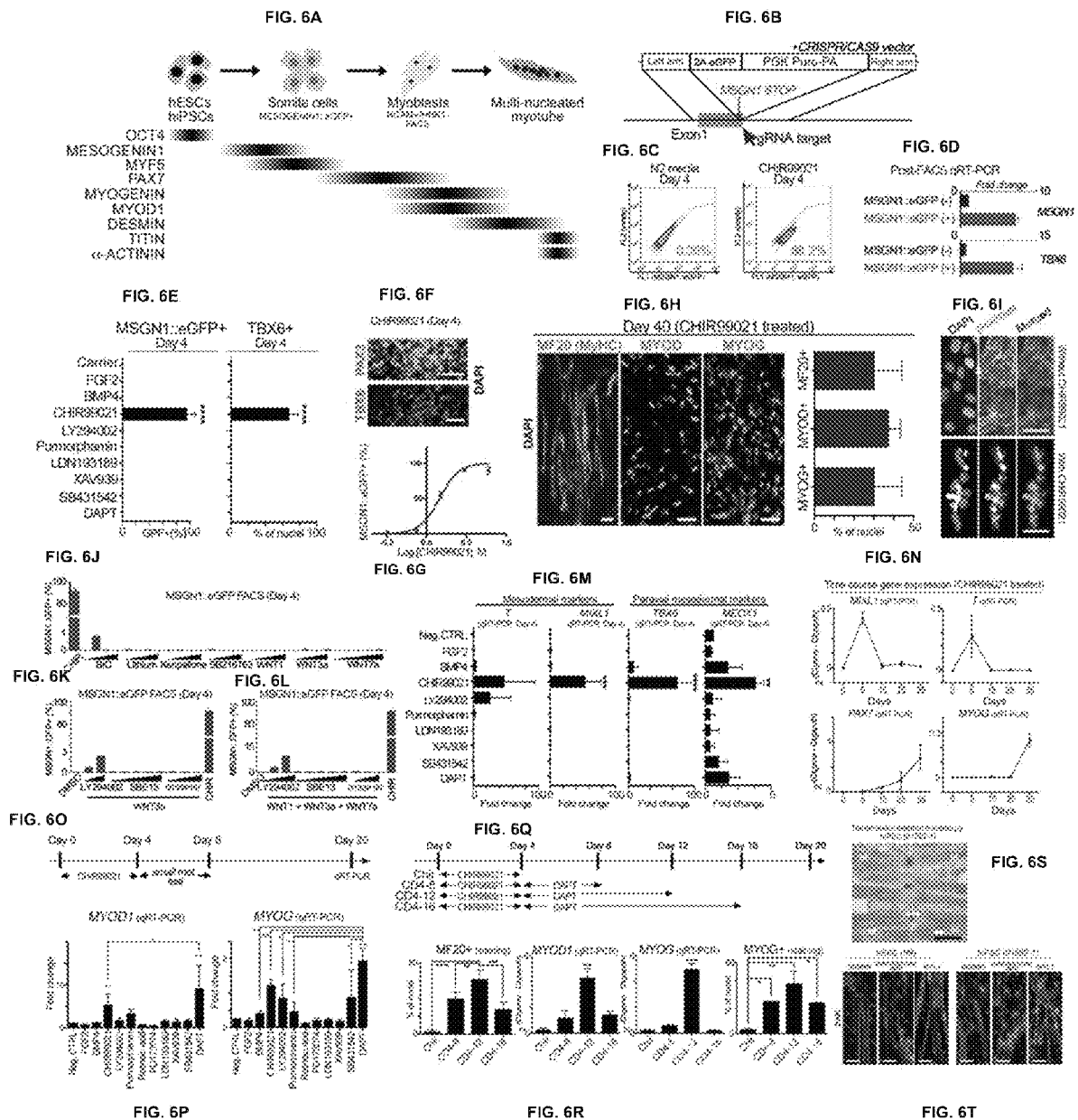

FIG. 7A
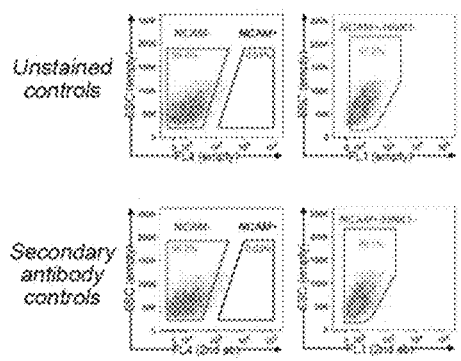
FIG. 7B
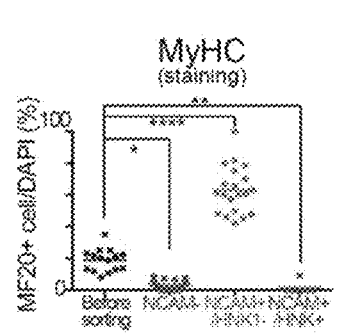
FIG. 7C
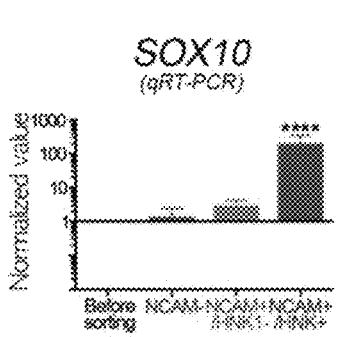
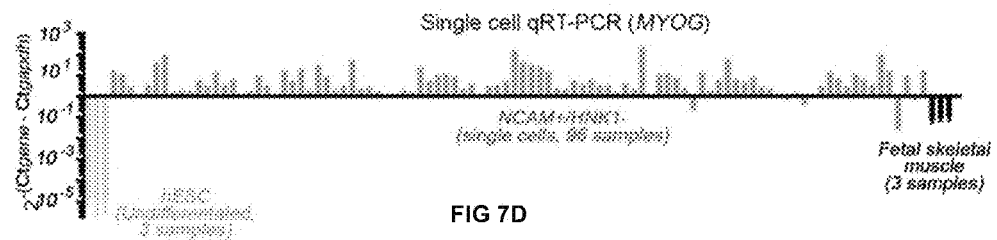
FIG 7D
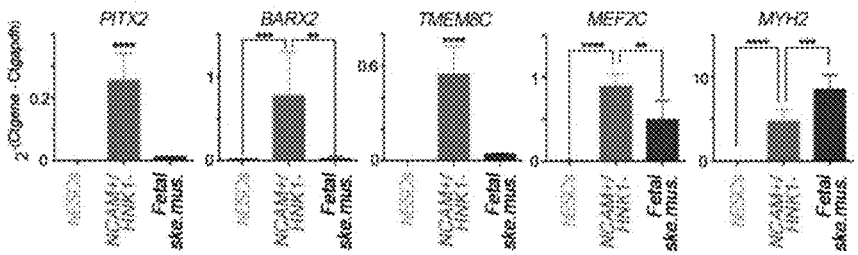
FIG 7E
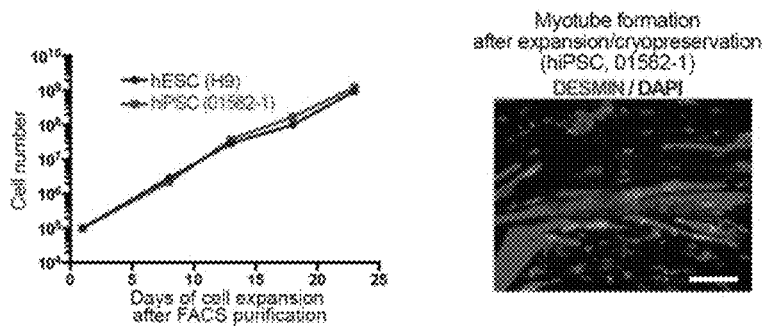
FIG. 7F          FIG. 7G

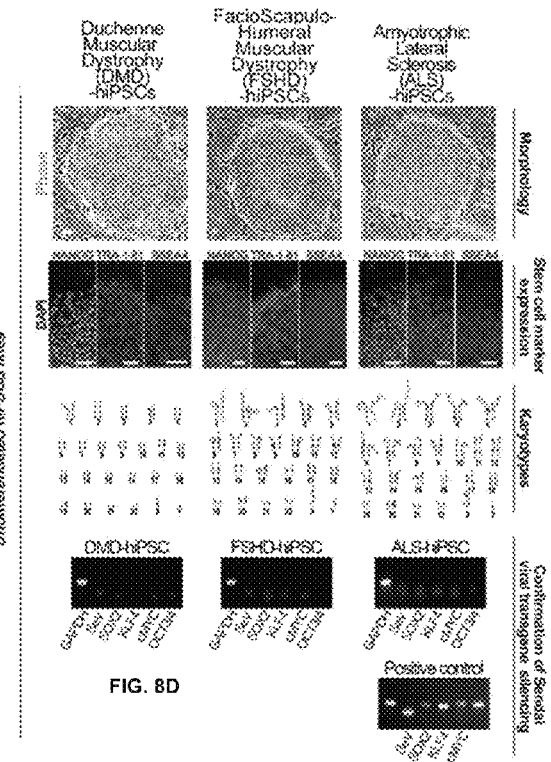
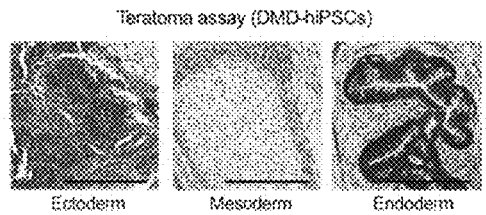
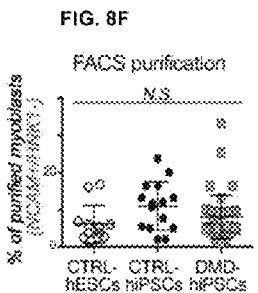
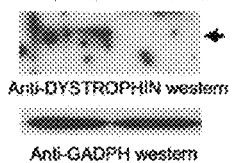
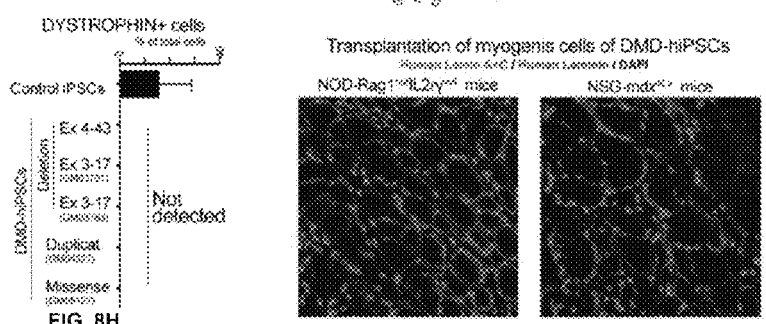
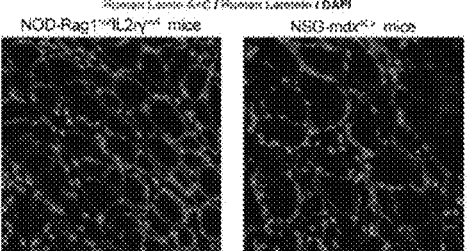
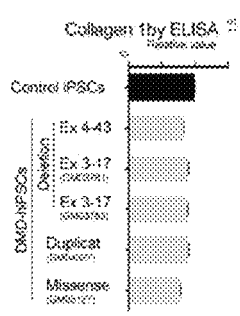
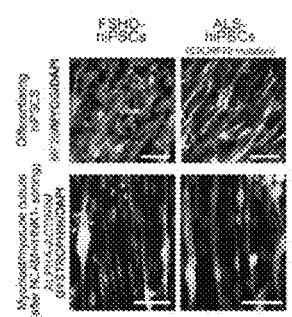
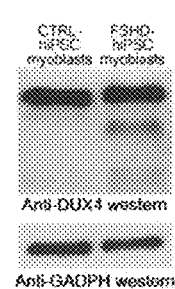
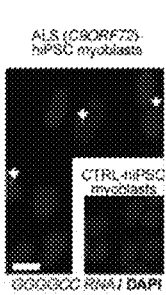

FIG. 9A
FIG. 9C
FIG. 9D
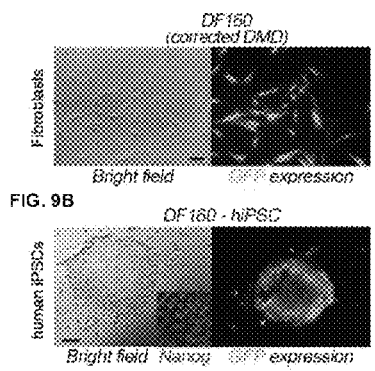
FIG. 9B
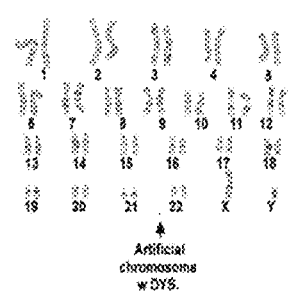
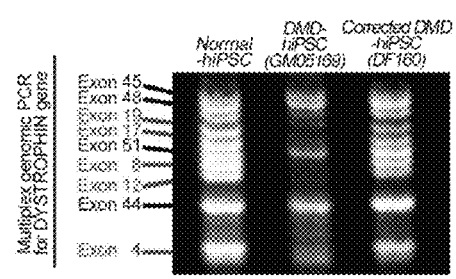
Transplantation of myogenis cells of DMD-hiPSCs
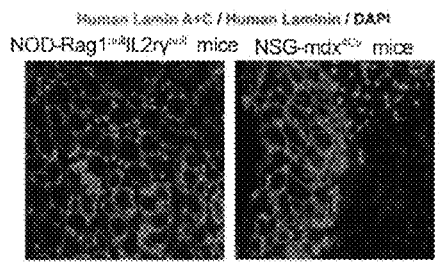
FIG. 9E
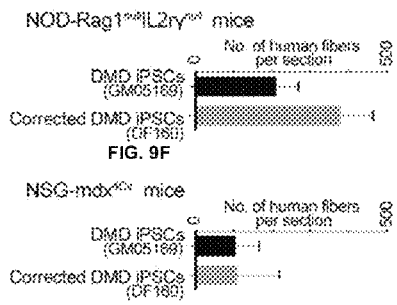
FIG. 9F
FIG. 9G
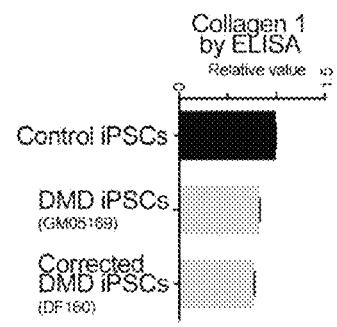
FIG. 9H

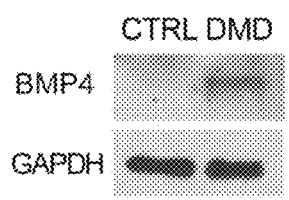
FIG. 10A
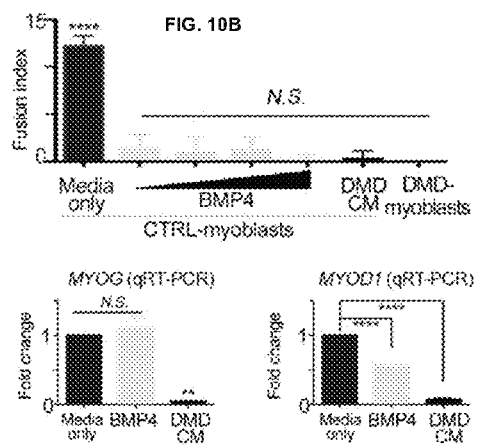
FIG. 10B
FIG. 10C
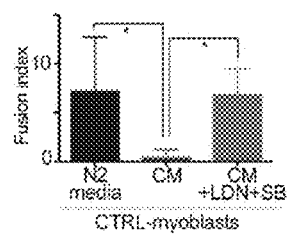
FIG. 10D

Figure 11 Table 1: Details of fibroblasts used for generation of DMD-hiPSC lines.

| ID in Coriell catalog | Description | Mutations | Age (yr) |
|---|---|---|---|
| GM05169 | DMD (deletion) | EX4-43DEL | 9 |
| GM05127 | DMD (non-sense mutation) | c.5533G>T, p.E1845X | 18 |
| GM04327 | DMD (duplication) | EX5-7DUP | 23 |
| GM03781 | DMD (deletion) | EX3-17DEL | 11 |
| GM03783 | DMD (deletion) | EX3-17DEL | 10 |

Figure 12 Table: Correlation between SPP expression and other 'potentially culprit genes'.

|  | r | 95% confidence interval | R squared | P (two-tailed) | P value summary | Significant? (alpha = 0.05) |
|---|---|---|---|---|---|---|
| SPP1 vs. BMP2 | 0.974 | 0.9071 to 0.9929 | 0.9486 | < 0.0001 | **** | Yes |
| SPP1 vs. BMP4 | 0.9851 | 0.9461 to 0.9959 | 0.9704 | < 0.0001 | **** | Yes |
| SPP1 vs. TGFB1 | -0.6537 | -0.8927 to -0.1278 | 0.4274 | 0.0211 | * | Yes |
| SPP1 vs. TGFB2 | -0.8336 | -0.9520 to -0.4978 | 0.6948 | 0.0008 | *** | Yes |
| SPP1 vs. TGFB3 | 0.9703 | 0.8945 to 0.9919 | 0.9415 | < 0.0001 | **** | Yes |
| SPP1 vs. TNFRSF21 | 0.7023 | 0.2151 to 0.9096 | 0.4932 | 0.0109 | * | Yes |
| SPP1 vs. EGF | 0.4151 | -0.2085 to 0.7987 | 0.1723 | 0.1797 | ns | No |
| SPP1 vs. CASPASE1 | 0.9839 | 0.9416 to 0.9956 | 0.968 | < 0.0001 | **** | Yes |
| SPP1 vs. CASPASE4 | 0.9397 | 0.7942 to 0.9833 | 0.8831 | < 0.0001 | **** | Yes |
| SPP1 vs. COL1A1 | -0.2073 | -0.6981 to 0.4161 | 0.04297 | 0.518 | ns | No |
| SPP1 vs. COL3A1 | 0.849 | 0.5365 to 0.9567 | 0.7208 | 0.0005 | *** | Yes |
| SPP1 vs. COL4A5 | 0.7275 | 0.2637 to 0.9181 | 0.5293 | 0.0073 | ** | Yes |
| SPP1 vs. COL4A6 | 0.8846 | 0.6312 to 0.9674 | 0.7826 | 0.0001 | *** | Yes |
| SPP1 vs. IL6 | 0.8993 | 0.6725 to 0.9717 | 0.8088 | < 0.0001 | **** | Yes |
| SPP1 vs. IL8 | 0.2953 | -0.3354 to 0.7433 | 0.08722 | 0.3514 | ns | No |

ISOLATION OF FUSION-COMPETENT MYOBLASTS AND THERAPEUTIC APPLICATIONS THEREOF RELATED TO MUSCULAR DYSTROPHY

CROSS-REFERENCE TO RELATED APPLICATIONS

This application is a 35 U.S.C. § 371 U.S. national entry of International Application PCT/US2016/065704, having an international filing date of Dec. 9, 2016, which claims the benefit of U.S. Provisional Application No. 62/266,181, filed Dec. 11, 2015, the content of each of the aforementioned applications is herein incorporated by reference in their entirety.

BACKGROUND OF THE INVENTION

One of the most common muscular dystrophies is Duchenne muscular dystrophy (DMD), affecting approximately 1 in 5,000 live male births. DMD is caused by mutations in DYSTROPHIN (Hoffman et al., 1987) and so far over 1,000 different sequence variations in the culprit gene have been discovered. Patients with DMD are heterogeneous in severity of disease due to specific DYSTROPHIN mutations as well as modifier genes as demonstrated by a wide range of loss of ambulation and end of life (Vo and McNally, 2015). Although zebra fish, mouse and dog models have provided DMD-related data on pathogenesis, it is generally recognized that each of these models have limitations (Kornegay et al., 2012; Partridge, 2013). A DMD study using mouse embryonic stem cells (mESCs) of a DMD mouse model has been published recently (Chal et al., 2015), but it is still questionable if any of the mESC-based studies can sufficiently model such varied severity in a mutation-dependent or patient-specific manner. Considering the high disease prevalence and severity, as well as a lack of meaningful therapies of most skeletal muscle disorders, it is critical to develop a human cellular model system.

Embryonic development has been successfully modeled in vitro with differentiating human pluripotent stem cells (hPSCs), including human embryonic stem cells (hESCs) and human induced pluripotent stem cells (hiPSCs), by modulating relevant signaling pathways via chemical compounds, as demonstrated in the neuroectodermal, cardiac and endodermal lineages (Borowiak et al., 2009; Burridge et al., 2014; Chambers et al., 2009; Di Giorgio et al., 2008). Combined with a strategy to isolate homogenous populations, disease-specific hiPSC-derived cells have often facilitated our understanding of pathogenesis of human genetic disorders by providing symptom-relevant cell types in a patient-specific manner (Chen et al., 2014; Kiskinis et al., 2014; Wainger et al., 2014), leading us to validate potential therapeutic small molecules with which to rescue in vitro phenotypes (Brennand et al., 2011; de Boer et al., 2014).

However, to date, such efforts have not been fully applied to the hiPSCs of muscular dystrophy, due to the absence of a successful strategy for isolating expandable functional myoblasts. Previous efforts towards the derivation of myogenic cells from hESCs and hiPSCs were based on the ectopic expression of myogenic transcription factors such as PAX3, PAX7 and MYOD1, by viral gene delivery (Darabi et al., 2012; Tedesco et al., 2012). Although this approach can produce certain myogenic cells, the random integration of viral DNA can jeopardize disease modeling, and might even mask any unknown potential disease phenotype. In addition, other previous protocols rely on animal-derived factors and require arduous long-term culture (over 4 months) (Barberi et al., 2007). More importantly, high-purity, disease-specific myoblasts need to be isolated and expanded to study their transcriptional profiles or functional deficits.

SUMMARY OF THE INVENTION

This application describes methods of isolating high purity myoblasts that are used to create novel DMD model systems using human induced pluripotent stem cells (hiPSCs), revealing concordant disease-related phenotypes with patient dependent variation, which are partially reversed by genetic and pharmacological approaches.

One embodiment of the present invention is a drug discovery method comprising the following steps: obtain one or more fibroblasts from a patient with muscular dystrophy; reprogram the one or more fibroblast into human induced pluripotent stem cells; direct the pluripotent stem cells into myoblasts in a mixture by incubating the pluripotent stem cells with CHIR99021 and DAPT; select myoblasts from the mixture by contacting myoblasts with NCAM(5.H1) antibody, HNK1 antibody or a combination thereof to form purified myoblasts; and treat purified myoblasts with one or more agent(s) to from rescued myoblasts so that the rescued myoblasts look more like a normal myoblast under similar conditions as the rescued myoblasts. The preferred agents of this invention are dual SMAD inhibitor compounds and a vector carrying the DYSTROPHIN gene. The preferred fibroblasts are patient fibroblasts from Coriell Cell Repository.

Another embodiment of the present invention is a method of treating a patient with muscular dystrophy comprising the following steps: obtain one or more fibroblasts from a patient with muscular dystrophy; reprogram the one or more fibroblast into human induced pluripotent stem cells; directed the pluripotent stem cells into myoblasts in a mixture by incubating the pluripotent stem cells with CHIR99021 and DAPT; select myoblasts from the mixture by contacting myoblasts with NCAM(5.H1) antibody, HNK1 antibody or a combination thereof to form purified myoblasts; and treat purified myoblasts with one or more agent(s) to from rescued myoblasts so that the rescued myoblasts look more like a normal myoblast under similar conditions as the rescued myoblasts; and transplant the rescued myoblasts into the patient with muscular dystrophy. The patient may have Duchene muscular dystrophy and the fibroblast may come from a skin biopsy. The preferred agents of this invention are dual SMAD inhibitor compounds and a vector carrying the DYSTROPHIN gene. It is preferred that myoblasts are selected from the mixture by contacting the myoblasts with NCAM(5.H1) antibody before contacting with HNK1 antibody. Another embodiment of the present invention is a method of isolating myoblasts comprising the following steps: obtain one or more fibroblasts from a patient with a disease; reprogram the one or more fibroblast into human induced pluripotent stem cells; directed the pluripotent stem cells into myoblasts in a mixture by incubating the pluripotent stem cells with CHIR99021 and DAPT; and select myoblasts from the mixture by contacting myoblasts with NCAM(5.H1) antibody, HNK1 antibody or a combination thereof to form purified myoblasts.

The term "DAPT" refers to a γ-secretase inhibitor that blocks Notch signaling.

The term 'dual SMAD inhibition' results from compounds including (LDN193189+SB431542=LDN+SB) that partially reverses the localization of phosphorylated SMAD (pSMAD) proteins.

The term "Dystrophin gene" refers a gene that encodes a rod-shaped cytoplasmic protein, and a vital part of a protein complex that connects the cytoskeleton of a muscle fiber to the surrounding extracellular matrix through the cell membrane. An example of a Homo sapiens dystrophin (DMD) transcript variant Dp427c, mRNA is NCBI Reference Sequence NM-000109.3 or NCBI accession number NM_000109.

The term "GSK-3β" refers to a glycogen synthase kinase 3 beta, for example, an enzyme in humans encoded by the GSK3β gene.

The term "Notch signaling" refers to the Notch signaling pathway that includes four different notch receptors, referred to as NOTCH1, NOTCH2, NOTCH3, and NOTCH4.

The term "SMAD" refers to one or more proteins (for example, SMAD1, SMAD2, SMAD3, SMAD4, SMAD5, SMAD6, SMAD7, SMAD8, SMAD9) currently believed to intracellular proteins that transduce extracellular signals.

The term "phosphorylated SMAD" or "pSMAD" proteins and expression levels of interleukin 6 and −8, and collagen 3 found in myoblasts.

The term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "patient" is a subject that has a disease such as muscular dystrophy.

By "disease" is meant any condition or disorder that damages or interferes with the normal function of a cell, tissue, or organ. Examples of diseases include muscular dystrophy.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A-1F illustrates characterization of myogenic cells derived from hPSCs. (A) Schematic illustration of myogenic specification of hPSCs with two chemical compounds. (B) Myogenic differentiation after CHIR99021 and DAPT treatment, determined (day 30) by expression of myosin heavy chain (MF20) and myogenic regulatory factors (MYOG). (C) Transmission electron micrograph showing sarcomeres in contractile, mature myotubes derived from hESCs (WA09). (D) (Left): Formation of numerous human, multinucleated myofibers by transplanted hPSC-derived skeletal muscle cells, four weeks after injection, confirmed with two human specific antibodies (LAMIN A+C and LAMININ). Inset shows enlarged image of a single myofiber. (Right): Co-expression of PAX7+ and hLAMIN A+C nucleus (white arrow) in human myofiber expressing hLAMININ. (E) Formation of hESC- and hiPSC-derived multinucleated myotubes expressing DYSTROPHIN, TITIN and α-ACTININ (with striation). (F) Quantification of DYSTROPHIN, TITIN and α-ACTININ expressing cells. n=3-10. Scale bars correspond to 50 μm, except A (500 ηm), and the insert of B (5 μm).

FIG. 2A-2F illustrates FACS purification of functional myoblasts cells. (A) Representative FACS plots for NCAM+/HNK1− cell population. (B-C) qRT-PCR confirming expression of MYOD1 and MYOG in post-sorted cells. (D) Clustered heat map of global gene expression values comparing NCAM+/HNK1−, human fetal skeletal muscle (18-19 weeks) and undifferentiated hESCs (hESC), using Partek program (Pearson correlation). Plot is rank-ordered with pluripotent-specific genes at the left, and skeletal muscle specific genes at the right. (E) Graph of the changes in gene expression levels as assessed by microarray analysis: increased in NCAM+/HNK1− (green), and decreased in undifferentiated hESCs populations (yellow) compared to each other. (F) Gene ontology (DAVID) analysis of up-regulated transcripts in NCAM+/HNK1− population. (****, P≤0.0001, One-way ANOVA followed by Newman-Keuls test), n=3-5. All values represent means and s.d.

FIG. 3A-3J illustrates DMD-hiPSC-derived myoblasts (DMD-myoblasts) show disease-related phenotypes. (A) Unsupervised clustered heat map of global gene expression values comparing control (CTRL) and DMD-myoblasts (after NCAM+/HNK1− purification) and gene ontology (DAVID and IPA/Ingenuity) analysis of transcripts that were upregulated in DMD as opposed to downregulated in control (left lower panel) transcripts in control myoblasts. (B) Heatmap of DMD qRT-PCR analysis with selected represented genes. The value is acquired after normalization by GAPDH value and fold change by the mean value of control hiPSCs. Each box represents different clones of the genotypes and biological repeats of the myoblast isolation. (C-G) Nuclear localization of phosphorylated SMAD (pSMAD) proteins and expression levels of interleukin 6 and −8, and collagen 3 found in myoblasts (after NCAM+/HNK1− purification) of multiple DMD-hiPSC lines. (H-I) Impaired myotube formation in DMD-myoblasts. (H) Representative images showing DESMIN staining. (I) Decreased level of fusion index (calculated as ratio of number of nuclei inside myotubes to the number of total nuclei×100 after myotube formation). (J) Pearson correlation heatmap among the genes listed in (B) shows the Pearson correlation coefficients of expression levels of each selected gene among DMD-myoblasts of five different patient hiPSC lines. Color key from brown to purple indicates correlation from low to high, respectively. The normalized expression values of those genes in were used for calculation of correlation matrix. *, P≤0.05; , P≤0.01; *, P≤0.001; ****, P≤0.0001, One-way ANOVA followed by Newman-Keuls test). N.S. not significantly different. n=3-11. All values represent means and s.d. Scale bars in H correspond to 50 μm.

FIG. 4A-4I illustrates genetic rescue of DMD-related features. (A) Introducing human artificial chromosome carrying full-length human DYSTROPHIN gene into fibroblasts (before GM05169, after introducing, DF160), followed by reprogramming into hiPSCs, and subsequent myogenic specification into corrected DMD-myoblasts. (B) Unsupervised clustered heat map of DMD qRT-PCR assay with corrected myoblasts (after NCAM+/HNK1− purification) showed reversed transcription profile, using Partek program (Euclidean distances as the distance measure). (C-G) Nuclear localization of phosphorylated SMAD (pSMAD) proteins and expression levels of interleukin 6 and −8, and collagen 3 found in myoblasts (after NCAM+/HNK1− purification) of rescued hiPSC line (DF160). Impaired myotube formation in DMD-myoblasts, determined at days 10 after myotube induction. (H-I) Increased fusion rate (H) and formation of myotubes from DF160 hiPSCs, expressing DYSTROPHIN, DESMIN and MYOSIN LIGHT CHAIN-1 (I). (*, P≤0.05; , P≤0.01; *, P≤0.001; ****, P≤0.0001, One-way ANOVA followed by Newman-Keuls test). n=3-6. All values represent means and s.d.

FIG. 5A-5H illustrates pharmacological inhibition of SMAD signaling facilitates formation of 'rescued' myotubes. (A-F) The 'dual SMAD inhibition' compounds (LDN193189+SB431542=LDN+SB) treatment partially reverses the localization of phosphorylated SMAD (pSMAD) proteins (A-B), expression levels of interleukin 6 (C) and −8 (D), collagen 3 (E), and myotube formation (F) in myoblasts (after NCAM+/HNK1− purification) of multiple DMD-hiPSC lines. (G-H) GFP-labeled corrected DMD-myoblasts were co-cultured with RFP-labeled (nuclei localized) DMD-myoblasts for formation of rescued myotubes as shown in two independent images with a single GFP-labeled myotube containing RFP-labeled nuclei (G). (H) Ratio of rescued myotube formation was significantly enhanced upon treatment with LDN+SB. The 'rescued fusion index' was calculated as the ratio of number of nuclei inside GFP+/RFP+ 'rescued' myotubes to the number of total nuclei×100 after myotube formation). (*, P≤0.05; , P≤0.01; *, P≤0.001; ****, P≤0.0001, One-way ANOVA followed by Newman-Keuls test, except F, t-test between DMSO and LDN+SB treatment per genotype). n=3-6. All values represent means and s.d. All scale bars correspond to 50 μm.

FIG. 6A-6T is related to FIG. 1 and illustrates early stage myogenic induction with two chemical compounds. (A) Illustration of four stages of myogenic differentiation from hESCs/hiPSCs varying in expression of nine marker genes. (B) Schematic image of target site (stop codon) for MESOGENIN1 (MSGN1)::eGFP donor construct and the guide RNA site. (C) Representative FACS plots (analyzed at day 4) for N2 media only and CHIR99021-treated MESOGENIN1::eGFP hESC line. (D) Transcriptional enrichment of MESOGENIN1 and TBX6 in MESOGENIN1::eGFP+ cells over MESOGENIN1::eGFP− cells, as determined by qRT-PCR after FACS-purification. (E) CHIR99021 significantly increases expression of MESOGENIN1 (MSGN1)::eGFP and TBX6+ cells. (F) Expression of PAX3 in CHRI99021-treated differentiated hESCs at day 4. (G) Dose-response curve of CHIR99021 on the MESOGENIN1::eGFP genetic reporter hESC line. (H) Expression of three skeletal muscle marker proteins (the heavy chain of myosin II (MF20), MYOD, and MYOGENIN) in CHIR99021 treated group (day 40). (I) CHIR99021 translocates β-CATENIN. (J) None of the four other GSKβ inhibitors nor recombinant WNT proteins recapitulate the effect of CHIR99021 on MESOGENIN1::eGFP expression. (K-L) LY294002, with either WNT3a, or WNT1+WNT3a+WNT7a, partially recapitulates the effect of CHIR99021. (M) CHIR99021 treatment induces expression of the general mesodermal (T and MIXL1) and paraxial mesodermal marker genes (TBX6, MEOX1), in the parental hESC line. (N) Time-course of gene expression, from day 0 to day 35, of skeletal muscle differentiation (CHIR99021 treated group) (qRT-PCR analysis). (O) Time scheme for testing small molecule treatment (day 4 to day 8), and the qRT-PCR analysis with MYOD1 and MYOG primers (at day 20). (P) Increased myogenic differentiation during different recombinant protein and chemical compound treatment between day 4 and day 8. (Q) Time scheme for testing duration of DAPT treatment (day 4 to day 16). (R) Enhanced myogenic differentiation in brief DAPT treatment (during day 4 to day 12), determined (day 30) by expression of myosin heavy chain (MF20) and myogenic regulatory factors (MYOD, MYOG) (E). (S) Transmission electron micrograph of 'twitching' skeletal muscle cells derived from hiPSCs (GM01582-1). (T) Formation of hESC- and hiPSC-derived multinucleated myotubes expressing DESMIN, α-SARCOGLYCAN and MYL1. (*, P≤0.05; , P≤0.01; *, P≤0.001; ****, P≤0.0001, One-way ANOVA followed by Newman-Keuls test). n=3-5. All values represent means and s.d. All scale bars correspond to 50 μm.

FIG. 7A-7G is related to FIG. 2 and illustrates the characterization of FACS-purified myoblasts. (A) Representative FACS plots for negative controls for NCAM and HNK1 antibodies. (B-C) Antibody staining and qRT-PCR analysis results of unsorted cells (before sorting), and in three FACS-purified subsets (NCAM−, NCAM+/HNK1− and NCAM+/HNK1+). (D) Single cell qRT-PCR of FACS-purified NCAM+/HNK1− individual cells (96 samples) with MYOG specific primer sets. As control, undifferentiated hESCs (Left) and human fetal skeletal muscle tissues (Right) are included in the graph. (E) Confirmatory qRT-PCR with specific primer sets. (F) Cell numbers of NCAM+/HNK1+ myoblasts derived from both hESC and hiPSC lines were expanded. (G) Representative image for myotube formation of expanded/cryopreserved myoblasts (hiPSC-derived). (*, P≤0.05; , P≤0.01; *, P≤0.001; ****, P≤0.0001, One-way ANOVA followed by Newman-Keuls test). n=3-4. All values represent means and s.d. Scale bar in A and J correspond to 500 ηm, and B to 50 μm.

FIG. 8A-8N is related to FIG. 3 and illustrates the characterization of multiple disease-specific hiPSC lines and disease-specific myoblasts. (A-B) Morphology (A), and pluripotency marker expression (B), in undifferentiated hiPSCs derived from primary cells of Duchenne muscular dystrophy (DMD), facioscapulohumeral muscular dystrophy (FSHD) and amyotrophic lateral sclerosis (ALS). (C) Representative karyotyping analysis showing normal karyotypes for each of the three disease hiPSC lines. (D) Absence of transgene expression with specific primer sets for Sendai virus gene (SeV), and four Yamanaka factors, in undifferentiated hiPSCs. Positive control sample (normal fibroblasts) was obtained 3 days after Sendai virus infection. (E) Teratoma assay of DMD-hiPSC lines showing multi-lineage differentiation potentials. (F) Comparable percentages of NCAM+/HNK1− (myoblast) populations derived from control-hESC, control-hiPSC and DMD-hiPSC lines. (G-H) Representative image of DYSTROPHIN western blotting (MANDYS1 antibody, 427 kDa) (G) and quantification of DYSTROPHIN expressing cells (H) of myoblast/myotube culture (after NCAM+/HNK1− purification) of DMD-hiPSC line. (I) Human specific antibody staining (human Lamin A+C and human Laminin) showing human myofiber formations in two mouse strains (NOD-Rag1$^{null}$IL2rγ$^{null}$ and NSG-mdx$^{4Cv}$ mice) receiving DMD-hPSC-derived myogenic cells. (J) Representative image showing cytoplasmic localization of pSMAD1/5 in control and nuclear localization of pSMAD proteins in DMD-hiPSC line (GM05169) NCAM+/HNK1− purified myoblasts. (K) Comparable levels of collagen 1 expression among DMD-myoblasts (after NCAM+/HNK1− purification). (L) Representative images of myogenic differentiation of ALS and FSHD hiPSC lines and myoblast/myotube culture (after NCAM+/HNK1− sorting), stained with MyHC (MF20), MYOGENIN, α-ACTININ and DYSTROPHIN antibodies. (M) Expression of DUX4-fl band (marked with black arrow, ~45 kDa) in FSHD-specific skeletal muscle cells, (lower panel for control GAPDH bands). (N) Presence of hexanucleotide repeats foci (indicated with white arrows) in ALS-specific myoblasts (C9ORF72 mutation). N.S. not significantly different, One-way ANOVA followed by Newman-Keuls test. n=3-6. All scale bars correspond to 50 µm, except L, 5 µm.

FIG. 9A-9H is related to FIG. 4 and illustrates the characterization of corrected DMD-hiPSCs and myoblasts. (A-B) Morphology of corrected DMD-myoblasts: (A) before and (B) after reprogramming. The transferred minichromosome contains eGFP construct, so DF160 fibroblasts and iPSC lines show eGFP expression. The inset shows the expression of NANOG in DF160 hiPSC line. (C) Representative karyotyping analysis shows normal karyotypes of corrected DMD-hiPSCs, and presence of artificial chromosome carrying human DYSTROPHIN (arrow). (D) Multiplex genomic DNA PCR result showing the reconstitution of DYSTROPHIN. (E-F) In vivo transplantation results. (E) Human specific antibody staining (human Lamin A+C and human Laminin) showing human myofiber formations in two mouse strains (NOD-Rag1$^{null}$IL2r$\gamma^{null}$ and NOD-SCID-IL2r$\gamma^{null}$-mdx$^{4Cv}$ mice) receiving genetically corrected DMD-hPSC-derived cells. (F-G) Quantification of the numbers of human fibers (human Laminin+ fibers) in two mouse strains, NOD-Rag1$^{null}$IL2r$\gamma^{null}$ (F) and NOD-SCID-IL2r$\gamma^{null}$-mdx$^{4Cv}$ mice (G). (H) Comparable level of collagen 1 expression (after NCAM+/HNK1− purification). (*, P≤0.05; *, P≤0.001; **, P≤0.0001, One-way ANOVA followed by Newman-Keuls test). n=3-9. All values represent means and s.d. All scale bars correspond to 50 µm.

FIG. 10A-10D is related to FIG. 5 and illustrates the effect of BMP4 on myoblasts and its pharmacological rescue. (A) Increased level of BMP4 expression in DMD-myoblasts than control myoblasts. (B-C) Inhibitive effect of conditioned media (CM, harvested after 24 hr incubation) from DMD-myoblasts on fusion index (B), and MYOG, and MYOD1 expression (C) of control hiPSC-derived myoblasts. Treatment with BMP4 (four different concentrations, 7.5 µg/ml to 25 µg/ml) recapitulated the effect of CM of DMD-myoblasts. (D) The decreased fusion index in DMD-CM-treated myoblasts was rescued by 'dual SMAD inhibition' compounds. (*, P≤0.05; *, P≤0.001; **, P≤0.0001, One-way ANOVA followed by Newman-Keuls test). n=3-5. All values represent means and s.d.

FIG. 11 is a table that illustrates details used for generation of DMD-hiPSC lines.

FIG. 12 is a table that illustrates the correlation between SPP expression and other 'potentially culprit genes'.

DETAILED DESCRIPTION OF THE INVENTION

The present invention was created through a number of discoveries. First, to harness the potential of hPSCs, a protocol to direct hPSCs into the skeletal muscle lineage was developed. As the somite is an intermediate stage between hPSCs and myogenic progenitor cells (Bentzinger et al, 2012; Dequeant and Pourquie, 2008) (FIG. 6A), a MESOGENIN1::eGFP reporter human embryonic stem cell (hESC) line was generated with the CRISPR/Cas9 system (Mali et al, 2013) (FIG. 6B-6D), because MESOGENIN1 is a genetic marker for the pre-somite mesoderm fate (Fior et al., 2012). Brief treatment (4 days after day 0 of differentiation) with CHIR99021 (an inhibitor of GSK-3β (Bennett et al, 2002)) significantly increased expression of MESOGENIN1::eGFP (80.8±11.3% cells out of total cells in a dish), TBX6 (67.4±10.4%) and PAX3 in a dose-dependent manner (FIG. 6E-6G) at day 4, and gave rise to myogenic cells expressing MyHC (MF20), MYOG and MYOD at day 40 (30.4±13.7%, 37.7±5.78%, 30.4±13.70%, respectively) (FIG. 6H). CHIR99021 seems to activate the canonical WNT signaling pathway, by confirmation of β-catenin translocation into the nucleus (FIG. 6I).

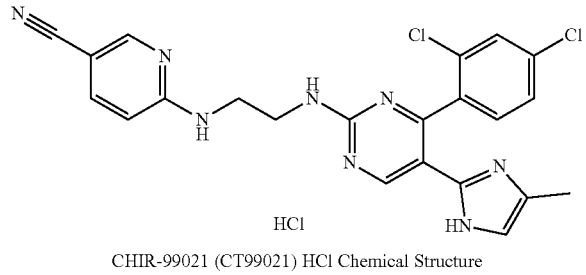 [SMILES: Cc1c[nH]c(-c2cnc(NCCNc3ccc(C#N)cn3)nc2-c2ccc(Cl)cc2Cl)n1 ; Cl]

CHIR-99021 (CT99021) HCl Chemical Structure

Further data analysis suggests that WNT activation and inhibition of the PI3K pathway (FIG. 6J-6L) is sufficient for induction of MESOGENIN1:eGFP from hPSCs, in agreement with results in other species (Wang et al., 2007). The effect of CHIR99021 could be readily repeated in the parental hESCs (FIG. 6M-6N). To increase the speed and efficacy of myogenic specification, DAPT (a γ-secretase inhibitor that blocks Notch signaling (Dovey et al., 2001), from day 4 to day 12) was determined to promote a robust and fast myogenic differentiation (FIG. 1A) (at day 30: MF20+, 63.6%±9.68%, and MYOGENIN+, 61.5%±11.0%, FIG. 1B and FIG. 6O-6R).

The resulting 'CHIR99021-DAPT culture' in defined N2 media (FIG. 1A), tested on multiple hiPSC lines (>10 different clones), consistently resulted in differentiation of myoblasts into multinucleated and spontaneously contractile myotubes, skeletal muscle cells derived from hESC (H9) and normal hiPSCs (GM01582, GM02036). The hESC- and hiPSC-derived myotubes in 'CHIR99021-DAPT culture' were further characterized by transmission electron microscopy. The spontaneously contracting myotubes showed a highly organized structure, including intact sarcomeres, with distinct Z-lines, M-lines and I-bands (FIG. 1C and FIG. 6S). To determine the in vivo engraftment potential, we transplanted the dissociated 'CHIR99021-DAPT culture' cells into the injured tibialis anterior (TA) muscle of NOD-Rag1$^{null}$IL2r$\gamma^{null}$ (NRG) mice. Six weeks after transplantation, immunohistochemisty with two human specific antibodies (human-specific Lamin A/C and human-specific Laminin) confirmed that the transplanted human myoblasts formed extensive myofibers (without tumor formation, n=33 mice) (left panel of FIG. 1D). Importantly, a small proportion human cells (human Lamin A/C+) were also observed to express PAX7 underneath a human Laminin basal lamina, indicating that some of the transplanted cells occupied the niche of adult muscle stem cells, known as satellite cells (right panel of FIG. 1D). In contrast, no expression of human antigens was detected in sham-transplanted control mice. To determine the presence of fusion-competent myoblasts, we re-plated the dissociated cells of the 'CHIR99021-DAPT culture' (day 25-30). Most of the attached and surviving cells were mono-nucleated at day 2 after re-plating, and could form multi-nucleated myotubes at day 10 after re-plating, with typical striations and expression of myotube marker proteins, DYSTROPHIN (35.5±6.4% cells were positive), TITIN (37.5±5.25%), and α-ACTININ (40.8±9.7%, sarcomeric organizations) (FIG. 1E-F and FIG. 6T).

Isolation of fusion-competent myoblasts should pave the way for disease modeling. As shown in FIG. 1E-1F and FIG. 6T, our 'CHIR99021-DAPT culture' culture contains fusion-competent myotubes as well as differentiated myotubes with well-organized sarcomeres. To isolate myoblasts, multiple different cell surface markers were tested to facilitate FACS purification of myoblasts in 'C-D culture'. Positive selection with the NCAM (5.1H11) antibody (Webster et al., 1988), combined with negative selection with the HNK1 antibody (FIG. 2A and S2A) enriched skeletal muscle progenitor cells. This determination was based upon significantly increased expression levels of MYOD1, MYOG, and MyHC (FIG. 2B-C and FIG. 7B-7C) in the NCAM+/HNK1− fraction over those of NCAM− or NCAM+/HNK1+ fractions. Furthermore, single-cell qRT-PCR showed that 98% of single NCAM+/HNK1− cells (95 out of 96) had higher expression of MYOG than a sample of human fetal skeletal muscle and undifferentiated hESCs (Figure FIG. 7D). To identify the global mRNA profiles, an unbiased gene expression analysis was performed, which showed a hierarchical clustering between the hPSC-derived NCAM+/HNK1− population and fetal skeletal muscle (18-19 weeks of gestation) over undifferentiated hESCs (FIG. 2D). Transcripts highly enriched in the NCAM+/HNK1− fraction included key markers of skeletal muscle structure development (Millay et al., 2013; Wang et al., 1979; Wohlgemuth et al., 2007) and key transcription factors (L'Honore et al., 2007; Martin et al., 1993) (FIG. 2E). Gene ontology analysis revealed statistically significant over-representation of GO terms among the up-regulated genes in the NCAM+/HNK1− fraction, including those of 'embryonic skeletal muscle development' ($p=4.52\times10^{-22}$), 'muscle structure system' ($p=2.10\times10^{-29}$), and 'muscle contraction' ($p=2.61\times10^{-24}$) (FIG. 2F). The gene expression array results were confirmed by qRT-PCR with primer sets for selected genes (FIG. 7E). The isolated NCAM+/HNK1− population is markedly proliferative during exposure to expansion-permissive conditions for 6 weeks, and easily expanded up to hundreds of million cells (a population doubling time for hESC and hiPSCs of 50.8±18.5 hours and 47.9±17.0 hours, respectively) (FIG. 7F). The hiPSC-derived myoblasts can be successfully cryopreserved and upon thawing maintain their myotube-forming potential (FIG. 7G).

To test if myoblast specification and isolation methods of the present invention can apply to hiPSCs derived from Duchenne muscular dystrophy (DMD) patients, patient-specific hiPSCs from five different genotypes were generated (FIG. 8A-8E). In order to find transcriptional changes between NCAM+/HNK1− cells (FIG. 8F) of DMD-hiPSC (GM05169, Exon4-43deletion) and the control (healthy)-hiPSC population, unbiased global transcription analysis, and subsequent gene ontology analysis were applied (FIG. 3A). The differentially up-regulated genes in NCAM+/HNK1− cells of DMD-hiPSC population (here after DMD-myoblasts) were largely classified into wound healing, inflammation, and signaling pathways. To validate these findings in different genotypes and mutations in DMD patient hiPSCs, a set of significantly up-regulated genes in DMD-myoblasts (fold-change≤2 fold; corrected p-value of 0.05, 17 over-represented genes in the five categories mentioned above) were chosen to perform qRT-PCR analysis. Using additional DMD-hiPSC lines with different mutations (two Exon3-17deletion, one Exon5-7duplication, and one nonsense mutation; at least 3 iPSC clones per genotypes), myoblasts were generated from each clone of DMD-hiPSC lines using the mentioned protocol above of myogenic specification and FACS purification procedures. No DYSTROPHIN protein was detectable in the DMD hiPSC-derived myoblasts using Western blot and immunohistochemistry (FIG. 8G-8H). In vivo transplantation experiments with two different mouse strains, NOD-Rag1$^{null}$IL2rγ$^{null}$ mice (immune-deficient healthy recipients) and NOD-SCID-IL2rγ$^{null}$-mdx$^{4Cv}$ mice (immuno-deficient mdx mice lacking dystrophin) (Arpke et al., 2013), show that myogenic culture of DMD-hiPSCs could participate in muscle regeneration processes after cardiotoxin injury (FIG. 8I). The different DMD-myoblasts each had varying levels of expression in the DMD qRT-PCR analysis, although they were all aberrantly expressed compared with control hiPSCs. In particular, all lines showed upregulated expression of BMP4 and TGFβ genes (FIG. 3B). Increased levels of BMP4 and TGFβ signaling were confirmed by a significantly increased nuclear localization of phosphorylated SMAD (pSMAD⅕ and ⅔) in DMD-myoblasts compared to control myoblasts (FIG. 3C-D and FIG. 8J). Increased protein expression levels of interleukin 6 and 8, and collagen 3 were observed in DMD-myoblasts, while that of collagen 1 remained comparable (FIG. 3E-G and FIG. 8K). Interestingly, myoblasts from individual DMD hiPSC lines show different patterns. For example, they all have higher levels of nuclear localized phospho-SMAD ⅕ and ⅔, but expression levels of interleukin 6 and 8, and collagen 3 are varied among different DMD-hiPSC lines. Furthermore, analysis of myotube formation as measured by the fusion index (the ratio of number of nuclei inside DESMIN+ myotubes to the number of total nuclei×100), showed that all the DMD-myoblasts from different DMD hiPSC lines had decreased myotube formation compared to that of control myoblasts ($p<0.0001$) (FIG. 3H-I). To test if this observation is specific to the DMD, hiPSC lines of facioscapulohumeral muscular dystrophy (FSHD) and amyotrophic lateral sclerosis (ALS, C9ORF72 mutation) (FIG. 8A) and myoblast cultures derived from hiPSC lines of FSHD- and ALS can form myotubes with expression of marker proteins (FIG. 8L-8N) were compared. Spontaneously twitching cells were often found during myogenic specification of ALS-hiPSCs, but spontaneously contracting cells during DMD-hiPSC differentiation (n=71 repeats) were not observed. The data of the present invention suggest that myoblasts of DMD-hiPSCs display transcriptional, translation, and functional in vitro phenotypes. After confirming such transcriptional and translational phenotypes of DMD-myoblasts, it was hypothesized there might be a significant correlation among the list of aberrantly expressed genes (FIG. 3B). A heatmap was generated from the gene-to-gene Pearson correlations for the 16 genes initially chosen from global transcriptional analysis (FIG. 3J). Among the positively co-correlated genes, SPP1, BMP4, CASPASE1, BMP2, and TGFβ3 formed the clearest cluster. Furthermore, additional correlation analysis (FIG. 12) confirmed the statistically significant correlation (p value, 0.0211~<0.0001) between SPP1 and the other 12 genes. Interestingly, SPP1 (=Osteopontin) has been shown as a potent genetic modifier of disease severity in DMD (Pegoraro et al., 2011; Zatz et al., 2014). These gene-to-gene correlation analyses suggest a potential role of SPP1/Osteopontin transcriptional cues for other genes involved in a particular signaling pathway, which could be related with the pathogenesis of DMD.

To restore the genetic deficiency of Exon 4-43 deletion of one of the DMD mutations, the human artificial chromosome (HAC) technique (Kazuki et al., 2010) was employed, as the conventional gene targeting approach is not feasible due to the size of the DNA to be delivered. Genetically corrected DMD fibroblasts were reprogrammed (GM05169 carry HAC with 2.4 Mb entire genomic DYSTROPHIN, renamed as DF160) into hiPSCs (FIG. 9A-9B). After confirmation of normal karyotype and presence of the HAC (FIG. 9C-9D), the myogenic culture of corrected DMD-hiPSCs was transplanted into NRG and NSG-mdx$^{4Cv}$ mice. We found comparable levels of human myofiber formation in in vivo environments (FIG. 9E-9G). FACS-purified myoblasts of the corrected DMD-hiPSCs (named 'corrected DMD-myoblasts') showed (FIG. 4A) reversed gene expression profiles in our DMD qRT-PCR assay (FIG. 4B), closer to that of control (healthy) myoblasts, but further from that of uncorrected DMD-myoblasts, in an unsupervised hierarchically clustering approach. The increased levels of nuclear localization of phosphorylated SMAD (pSMAD) and expression of interleukin 6 and 8, and collagen 3 were reversed in the corrected DMD-myoblasts (NCAM+/HNK1− cells) (FIG. 4C-G), while expression level of collagen 1 remains comparable (FIG. 9H). More importantly, the fusion index of the corrected DMD-myoblasts was significantly higher (p<0.0001) than that of DMD-myoblasts, but it was significantly lower than that of control myoblasts (p<0.05) (FIG. 4H). Unlike uncorrected DMD-hiPSCs that did not express DESMIN (FIG. 4H), the multinucleated myotubes of corrected DMD-hiPSCs express DYSTROPHIN, DESMIN and MYOSIN LIGHT CHAIN-1 (FIG. 4I).

To find pharmacological rescue of the in vitro phenotypes, aberrant BMP and TGFβ signaling indicated by increased nuclear localization of pSMAD proteins in DMD-myoblasts (FIG. 3C-3D) was studied. Increased levels of BMP4 in the conditioned media (CM) of DMD-myoblasts (FIG. 10A) was detected. Furthermore, the effect of the CM of DMD-myoblasts on the control myoblasts was tested and found significantly decreased myotube formation of control myoblasts and significantly decreased expression levels of MYOG and MYOD1 of control myoblasts (FIG. 10B-C) than those of the CM of control-myoblasts. The effect of CM of DMD-myoblasts was reproduced by treatment with BMP4 protein in the culture media, which was reversed by treatment with 'dual-SMAD' inhibition compounds (FIG. 10D) (LDN+SB: LDN193189 and SB431542).

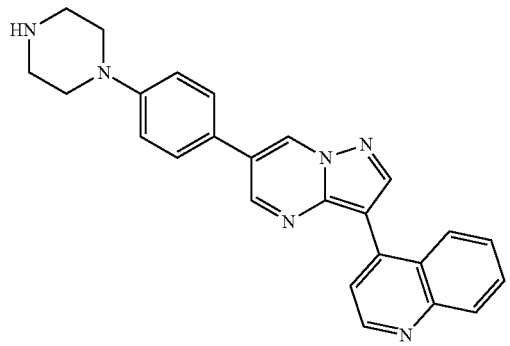

LDN-193189

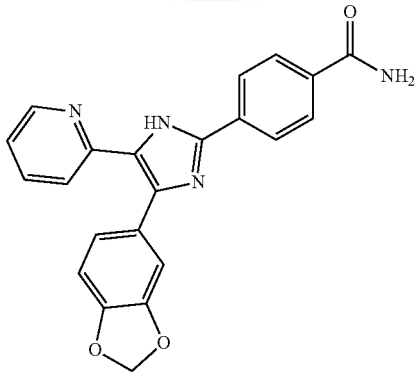

SB431542

These data suggest that pharmacological rescue can mitigate the effects of inhibitory cytokines in DMD-myoblasts. This hypothesis was tested in DMD-myoblasts, and found that treatment with the 'dual-SMAD' inhibition compounds (LDN+SB) reversed the level of increased nuclear localization of pSMAD protein and expression of interleukin 6 and 8, and collagen 3 (FIG. 5A-5E). In addition, the LDN+SB treatment can rescue the fusion defects in DMD-myoblasts with 4 out 5 mutations (FIG. 5F), but did not reverse the fusion defects in DMD-myoblasts with Exon5-7 duplication (GM04327). These data show that pharmacological inhibition of SMAD signaling intervention can rescue DMD-related phenotypes in DMD-myoblasts of some patients, and restore the functional deficit, albeit with less efficiency.

Next, we determined whether the genetically corrected DMD-myoblasts can fuse with DMD-myoblasts in vitro, thus mimicking the microenvironment of a DMD patient receiving a transplant of genetically correct autologous myoblasts. Genetically corrected DMD-myoblasts (DF160) were transfected with eGFP (marking the cytoplasm as green), and uncorrected DMD-myoblasts (GM05169) were transfected with nuclear RFP (marking the nuclei as red), then the two cell lines were co-cultured, permitting myotube fusion (FIG. 5G). Some of the GFP+ myotubes contained RFP+ nuclei, demonstrating the formation of 'rescued' myotubes arising from fusion of corrected DMD-myoblasts and non-corrected DMD-myoblasts. The number of nuclei participating in the formation of 'rescued' myotubes was calculated with a new index, 'rescued fusion index' (calculated as the ratio of number of nuclei inside GFP+/RFP+ 'rescued' myotubes to the number of total nuclei×100 after myotube formation). Importantly, the rescued fusion index between corrected DMD-myoblasts and non-corrected DMD-myoblasts was significantly increased upon treatment with 'dual-SMAD' inhibition compounds (FIG. 5H).

The myogenic isolation process of the present invention employing two small molecules (CHIR99021 and DAPT) was shown to be sufficient to direct multiple hPSC lines (13 different genotypes, including three different disease-specific hiPSC lines) into myogenic lineages in approximately 30 days. The hPSC-derived myoblasts can be isolated by FACS, and their functional and molecular characterization confirmed their myogenic properties, such as authentic myogenic transcriptional program, formation of striated contractile myofibers, highly organized ultra-structure, and in vivo engraftment capability. Furthermore, this system was readily applied to DMD-specific hiPSCs with multiple genetic variations (three different deletion types, one duplication, and one non-sense mutation), successfully generating DMD-myoblasts presenting DMD-related phenotypes including altered transcriptional profiles, aberrant intracellular signaling, and defective myotube formation. These DMD phenotypes were partially reversed by genetic and pharmacological approaches, resulting in the formation of 'rescued' myotubes between DMD-myoblasts and their genetically corrected isogenic ones. The myoblast isolation and purification process of the present invention have enabled the discovery of humanized DMD model systems of the present invention to study multiple aspects of disease, specifically DMD pathogenesis.

The MESOGENIN1::eGFP reporter hESC line used in the present invention, generated by CRISPR/Cas9-mediated gene-targeting, allowed the identification of the mechanism of activation of the WNT pathway and inhibition of the PI3K pathway are needed for directing hESCs/hiPSCs into somite stage (MESOGENIN1::eGFP+ population); suggesting possible off-target effects of CHIR99021. The present invention also demonstrates that inhibition of the Notch signaling pathway is critical to increase and accelerate the myogenic program of hESC/hiPSC-derived somite cells showing the significance of Notch signaling on the fate decision process of somite cells.

The myotubes generated using one or more of the methods of the present invention were often found spontaneously contract in vitro and possessed a highly systematized ultrastructure resembling that of in vivo skeletal muscle assemblies. Indeed, in vivo experiments with the myogenic cells of hESCs/hiPSCs demonstrated that they efficiently participated in the process of murine muscle regeneration. Importantly, a few transplanted human cells could be found in the satellite cell niche, beneath the basal lamina and expressing PAX7. Another important finding is the establishment of an isolation strategy of expandable myoblasts from a heterogeneous hiPSCs culture. After approximately 30 days of myogenic specification, it was observed that the culture dishes contained different types of cells, including spontaneously twitching myofibers/myotubes, myoblasts, neurons and fibroblasts. Among this diversity of cells, only some of them were mono-nucleated myoblasts, which can be FACS-purified by using NCAM and HNK1 antibodies. This novel FACS-purification strategy was readily applied to multiple hiPSC lines, and the yields were comparable among different genotypes of hESCs/hiPSCs, including DMD-hiPSCs. Furthermore, the FACS-purified myoblasts can be expanded up to the hundreds of million cells, and easily cryo-preserved without losing fusion competence. Combined with the xeno-free culture condition (defined media condition and compound based specification), our protocol could be extended to a large-scale compound screening efforts and myoblast transplantation to patients.

The DMD phenotypes of the myoblasts produced from the methods of the present invention, including increased levels of BMP4 and TGF signaling, aberrant expression of interleukins and the collagen genes, and fusion defects, agree with previous studies of animal models of DMD and of a myoblast culture derived from a biopsy taken from a DMD patient (Cesana et al., 2011; Hartel et al., 2001; Jasmin et al., 1984; Ng et al., 2012; Porter et al., 2002). Importantly, upon 'dual SMAD' inhibition, genetically corrected DMD-myoblasts can form significantly increased numbers of 'rescued' myotubes containing nuclei of DMD-myoblasts. This 'rescued' myotube culture can be useful in myoblast transplantations.

DMD-myoblasts isolated from four patients using the methods of the present invention were rescued upon pharmacological 'dual SMAD' inhibition, but not the one with Exon5-7 duplication (GM04327). These data suggest patient-specific disparities in DMD manifestation might be modeled in cell culture. It remains to be determined why DMD-myoblasts of each patient display varied phenotypes and responses to pharmacological rescue, but these data could be relevant to the varied severity/progression of the disease symptoms among patients and potentially the response to different therapeutic reagents (Pegoraro et al., 2011; Zatz et al., 2014). For example, the present invention shows that SPP1/Osteopontin expression levels in DMD-myoblasts of different patients are significantly correlated with most of the elevated expression levels of the 'pathogenic candidate genes'. Moreover, in vivo experiments of the present invention show myogenic cells of DMD-hiPSCs can form human myofibers in healthy and mdx mouse models. The in vitro human model of DMD-myoblasts of the present invention has been demonstrated to model the cellular condition of DMD patient pathology and will be useful for understanding patient-specific disparities.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES/METHODS

Cell Culture

Human embryonic stem cells (H9, WiCell) and human induced pluripotent stem cells were cultured using standard protocols. The hESC lines and hiPSC lines were cultured with mouse embryonic fibroblasts (MEFs) (GlobalStem, or AppliedStemCell) pre-plated at 12-15,000 cells/cm². Medium contained DMEM/F12, 20% knockout serum replacement, 1 mM L-glutamine, 100 µM MEM non-essential amino acids, and 0.1 mM β-mercaptoethanol. Ten ng/ml of FGF-2 was added after sterile filtration, and cells were fed daily, and passaged weekly, using 6 U/mL dispase or mechanically.

Generation of Human iPSCs

The ALS patient fibroblasts (JH078 (C9ORF72) and GO013 (SOD1 A4V)) were collected at Johns Hopkins Hospital with patient consent (IRB protocol: "Skin biopsies to generate cell lines for study of Amyotrophic Lateral Sclerosis", NA_00021979). Primary FSHD myoblasts (05Bdel) were obtained from the Senator Paul D. Wellstone Muscular Dystrophy Cooperative Research Center for FSHD Research. Other fibroblasts (FIG. 11) were purchased from Coriell, with appropriate Material Transfer Agreement documents. Genetically corrected DMD fibroblasts (DF160) were previously generated by transferring the HAC with entire DYSTROPHIN gene into DMD fibroblasts (GM05169). Human cells were cultured in DMEM media containing 10% FBS. Fibroblasts were plated onto 24-well plates, then reprogrammed by using CytoTune®-iPS Sendai Reprogramming Kit (Invitrogen) using our standard protocol. After 9 days, cells were put on MEF feeder medium with Y-27632, then grown.

Myogenic Differentiation of hESCs and hiPSCs

For myogenic differentiation, hESCs/hiPSCs were rendered to single cells using Accutase® solution, and plated on gelatin for 10 minutes to remove MEFs. Non-adherent cells were collected and plated on Geltrex™ treated dishes, at a density of 1.5×105 cells per well of a 24-well plate, in the presence of MEF-conditioned N2 media containing 10 ng/ml of FGF-2 and 10 µM of Y-27632 (Cayman Chemical Co.) (day 0). The N2 medium, described in detail, contains DMEM/F12 powder, glucose, sodium bicarbonate, insulin, putrescine, progesterone, sodium selenite, and transferrin. From the next day (day 1), media was changed at every other day. BIO (30 nM-250 nM), lithium chloride (20 µM-20 mM), Kenpallone (1 µM-10 µM), SB 216763 (1 µM-10 µM), WNT-1 (10 ng/ml-100 ng/ml), WNT-3A (10 ng/ml-100 ng/ml), WNT-7A (10 ng/ml-100 ng/ml), SBE13 hydrochloride (0.1 nM-10 µM), and OTSSP167 hydrochloride (0.1 nM-10 nM) were tested during day 1 to day 4, as well as during day 4 to day 8. Final concentrations of CHIR99021 and DAPT treatment are 3 µM and 10 µM, respectively.

The invention claimed is:

1. A method of producing a myoblast cell that expresses NCAM and does not express HNK1, comprising:
   (a) providing a pluripotent stem cell in a Dulbecco's Modified Eagle Medium (DMEM) that comprises putrescine and progesterone;
   (b) contacting the cell of step (a) with CHIR99021 in the DMEM for 4 days; and thereafter
   (c) contacting the cell of step (b) with DAPT (tert-Butyl (S)-{(2S)-2-[2-(3,5-difluorophenyl)acetamido] propanamido}phenylacetate) in the DMEM, thereby producing a myoblast cell.

2. The method of claim 1, wherein the pluripotent stem cell is an induced pluripotent stem cell.

3. The method of claim 2, wherein the induced pluripotent stem cell was prepared from a fibroblast isolated from a patient having muscular dystrophy.

4. The method of claim 3, further comprising genetically altering the myoblast cell to express DYSTROPHIN.

5. The method of claim 4, further comprising treating the myoblast cell with a SMAD inhibitor.

6. The method of claim 5, wherein the SMAD inhibitor comprises LDN-193189 and SB431542.

7. The method of claim 1, wherein the DMEM further comprises glucose, sodium bicarbonate, insulin, sodium selenite, and transferrin.

* * * * *